US009668959B2

(12) United States Patent
Madi et al.

(10) Patent No.: US 9,668,959 B2
(45) Date of Patent: Jun. 6, 2017

(54) A3 ADENOSINE RECEPTOR LIGANDS FOR MODULATION OF PIGMENTATION

(71) Applicant: ORADIN PHARMACEUTICAL LTD., Tel Aviv (IL)

(72) Inventors: Lea Levana Madi, Rishon Lezion (IL); Rafi Korenstein, Tel Aviv (IL)

(73) Assignee: ORADIN PHARMACEUTICAL LTD., Tel Aviv (IL)

( * ) Notice: Subject to any disclaimer, the term of this patent is extended or adjusted under 35 U.S.C. 154(b) by 0 days.

(21) Appl. No.: 14/941,108

(22) Filed: Nov. 13, 2015

(65) Prior Publication Data
US 2016/0136079 A1    May 19, 2016

Related U.S. Application Data

(62) Division of application No. 13/386,339, filed as application No. PCT/IL2010/000576 on Jul. 20, 2010, now Pat. No. 9,199,102.

(60) Provisional application No. 61/227,079, filed on Jul. 21, 2009.

(51) Int. Cl.
| | | |
|---|---|---|
| *A61K 8/00* | (2006.01) | |
| *A61K 8/60* | (2006.01) | |
| *A61K 8/49* | (2006.01) | |
| *A61K 31/4418* | (2006.01) | |
| *A61K 31/7076* | (2006.01) | |
| *A61Q 19/02* | (2006.01) | |
| *A61Q 19/04* | (2006.01) | |

(52) U.S. Cl.
CPC .............. *A61K 8/60* (2013.01); *A61K 8/4926* (2013.01); *A61K 8/4933* (2013.01); *A61K 8/606* (2013.01); *A61K 31/4418* (2013.01); *A61K 31/7076* (2013.01); *A61Q 19/02* (2013.01); *A61Q 19/04* (2013.01); *A61K 2800/70* (2013.01)

(58) Field of Classification Search
CPC .... A61K 8/4926; A61K 8/4933; A61K 8/606; A61K 31/4418; A61K 8/60; A61K 2800/70; A61K 31/7076; A61Q 19/02; A61Q 19/04
See application file for complete search history.

(56) References Cited

U.S. PATENT DOCUMENTS

| | | | |
|---|---|---|---|
| 5,262,153 A | 11/1993 | Mishima | |
| 5,554,359 A | 9/1996 | Fuller | |
| 5,602,259 A | 2/1997 | Boo | |
| 5,747,006 A | 5/1998 | Dornoff | |
| 5,905,091 A | 5/1999 | Fuller | |
| 5,965,618 A | 10/1999 | Perricone | |
| 5,980,904 A | 11/1999 | Leverett | |
| 5,998,423 A * | 12/1999 | Manneth | A61K 8/606 514/265.1 |
| 6,068,834 A | 5/2000 | Kvalnes | |
| 6,077,503 A | 6/2000 | Dornoff | |
| 6,177,444 B1 | 1/2001 | Baraldi | |
| 6,194,449 B1 | 2/2001 | Baraldi | |
| 6,323,214 B1 | 11/2001 | Baraldi | |
| 6,448,253 B1 | 9/2002 | Baraldi | |
| 7,019,029 B2 | 3/2006 | Perricone | |
| 7,064,112 B1 | 6/2006 | Fishman | |
| 7,141,553 B2 | 11/2006 | Fishman | |
| 7,435,740 B2 | 10/2008 | Baraldi | |
| 7,465,715 B2 | 12/2008 | Fishman | |
| 7,470,698 B2 | 12/2008 | Baraldi | |
| 7,511,133 B2 | 3/2009 | Baraldi | |
| 9,241,893 B2 * | 1/2016 | Caetano | A61K 8/97 |
| 2002/0115635 A1 | 8/2002 | Fishman | |
| 2002/0165197 A1 * | 11/2002 | Fishman | A61K 31/52 514/46 |
| 2004/0067932 A1 | 4/2004 | Borea | |
| 2005/0250729 A1 | 11/2005 | Baraldi | |
| 2006/0178385 A1 | 8/2006 | Baraldi | |
| 2007/0225335 A1 * | 9/2007 | Bloomfield | C07D 231/12 514/341 |
| 2007/0299032 A1 | 12/2007 | Ehama | |
| 2008/0044439 A1 | 2/2008 | David | |

FOREIGN PATENT DOCUMENTS

| | | |
|---|---|---|
| WO | 98/15276 A1 | 4/1998 |
| WO | 2006/015860 A2 | 2/2006 |
| WO | 2008/023362 | 2/2008 |

OTHER PUBLICATIONS

Baraldi and Borea (2000) New potent and selective human adenosine A(3) receptor antagonists. Trends Pharmacol Sci 21(12): 456-9.
Boissy et al., (2005) DeoxyArbutin: a novel revesible tyrosinase inhibitor with effective in vivo skin lightening potency. Exp Dermatol 14(8): 601-608.
Cardinali et al., (2005) Keratinocyte growth factor promotes melanosome transfer to keratinocytes. J Invest Dermatol 125(6): 1190-1199.
Choi et al., (2008) Whitening activity of luteolin related to the inhibition of cAMP pathway in alpha-MSH-stimulated B16 melanoma cells. Arch Pharm Res 31(9): 1166-1171.

(Continued)

*Primary Examiner* — Suzanne Ziska
(74) *Attorney, Agent, or Firm* — Rothwell, Figg, Ernst & Manbeck, P.C.

(57) ABSTRACT

The present invention relates to compositions and methods for modulating melanin production, secretion and/or accumulation in human skin cells. In particular, the present invention relates to the use of A3 adenosine receptor antagonists in compositions and methods for the treatment and amelioration of hyper-pigmentation conditions and for the lightening of skin, and to the use of A3 adenosine receptor agonists in compositions and methods for the treatment and amelioration of hypo-pigmentation conditions and for the tanning of skin.

9 Claims, 13 Drawing Sheets

(56) References Cited

OTHER PUBLICATIONS

Choi et al., (2014) Pleiotrophin inhibits melanogenesis via Erk1/2-MITF signaling in normal human melanocytes. Pigment Cell Melanoma Res 28(1): 51-60.
Draelos (2007) Skin lightening preparations and the hydroquinone controversy. Dermatol Ther 20(5): 308-313.
Englaro et al., (1998) Inhibition of mitogen-activated protein kinase pathway triggers B16 melanoma cell differentiation. J Biol Chem 273(16): 9966-9970.
Forsythe and Ennis (1999) Adenosine, mast cells and asthma. Inflam Res 48(6): 301-307.
Fredholm et al., (2000) Naunyn Schmiedebergs Arch Pharmacol. 362(4-5): 364-374.
Fredholm et al., (2001) Comparison of the potency of adenosine as an agonist at human adenosine receptors expressed in Chinese hamster ovary cells. Biochem Pharmacol 61(4): 443-8.
Fredholm et al., (2001) International Union of Pharmacology. XXV. Nomenclature and classification of adenosine receptors. Pharmacol Rev 53(4): 527-552.
Hakozaki et al., (2013) A regulator of ubiquitin-proteasome activity, 2-hexyldecanol, suppresses melanin synthesis and the appearance of facial hyperpigmented spots. Br J Dermatol 169 (Suppl 2): 39-44.
Heitman et al., (2009) A series of 2,4-disubstituted quinolines as a new class of allosteric enhancers of the adenosine A3 receptor. J Med Chem 52: 926-31.
Hunt et al., (1994) alpha-melanocytes stimulating hormone and its analogue Nle4DPhe7 alpha-MSH affect morphology, tyrosinase activity and melanogenesis in cultured human melanocytes. J Cell Sci 107(pt 1): 205-211.
Im et al., (1998) Activation of cyclic AMP pathway by alpha-melanotropin mediates the response of human melanocytes to ultraviolet B radiation. Cancer Res 58(1): 47-54.
Jacobson and Gao (2006) Adenosine receptors as therapeutic targets. Nature Rev Drug Discov 5(3): 247-64.
Jacobson et al., (1995) A3-adenosine receptors: Design of selective ligands and therapeutic prospects. Drugs of the Future 20(7): 689-699.
Jacobson et al., (1995) Structure-activity relationships of 9-alkyladenine and ribose-modified adenosine derivatives at rat A3 adenosine receptors. J Med Chem 38(10): 1720-35.
Jacobson et al., (1997) Pharmacological characterization of novel A3 adenosine receptor-selective antagonists. Neuropharmacology 36(9): 1157-65.
Jacobson et al., (1998) A3 adenosine receptors: Protective vs. damaging effects identified using novel agonists and antagonists. Drug Dev Res 45(3-4): 113-124.
Jeong (2008) Development of A3 adenosine receptor ligands. Nucleic Acids Symp Ser (Oxf) (52): 79-80.
Ji et al., (1996) Interactions of flavonoids and other phytochemicals with adenosine receptors. J Med Chem 39: 781-8.
Jiang et al., (1996) 6-phenyl-1,4-dihydropyridine derivatives as potent and selective A3 adenosine receptor antagonists. J Med Chem 39: 4667-75.
Jiang et al., (1997) Structure-activity relationships of 4-(phenylethynyl)-6-phenyl-1,4-dihydropyridines as highly selective A3 adenosine receptor antagonists. J Med Chem 40: 2596-608.
Karton et al., (1996) Synthesis and Biological Activities of Flavonoid Derivatives as A3 Adenosine Receptor Antagonists. J Med Chem 39: 2293-2301.
Kim et al., (1996) Derivatives of the triazoloquinazoline adenosine antagonist (CGS15943) are selective for the human A3 receptor subtype. J Med Chem 39: 4142-48.
Kohno et al., (1996) Activation of A3 adenosine receptors on human eosinophils elevates intracellular calcium. Blood 88(9): 3569-74.
Lebonvallet et al., (2010) The evolution and use of skin explants: potential and limitations for dermatological research. Eur J Dermatol 20(6): 671-84.
Lee et al., (2007) Mechanisms of melanogenesis inhibition by 2,5-dimethyl-4-hydroxy-3(2H)-furanone. Br J Dermatol 157(2): 242-248.
Li et al., (1999) Synthesis, CoMFA analysis, and receptor docking of 3,5-diacyl-2, 4-dialkylpyridine derivatives as selective A3 adenosine receptor antagonists. J Med Chem 42: 706-21.
Liang and Jacobson (1998) A physiological role of the adenosine A3 receptor: sustained cardioprotection. Proc Natl Acad Sci U.S.A. 95(12): 6995-6999.
Linden (2001) Molecular approach to adenosine receptors: receptor-mediated mechanisms of tissue protection. Annu Rev Pharmacol Toxicol 41: 775-87.
Okamura et al., (2004) Structure-activity relationships of adenosine A3 receptor ligands: new potential therapy for the treatment of glaucoma. Bioorg Med Chem Lett 14(14): 3775-9.
Park et al., (2014) Wnt inhibitory factor (WIF)-1 promotes melanogenesis in normal human melanocytes. Pigment Cell Melanoma Res 27(1): 72-81.
Salvatore et al., (2000) Disruption of the A(3) adenosine receptor gene in mice and its effect on stimulated inflammatory cells. J Biol Chem 275(6): 4429-4434.
Sato et al., (2008) Down-regulation of tyrosinase expression by acetylsalicylic acid in murine B16 melanoma. Biol Pharm Bull 31(1): 33-37.
Siddiqi et al., (1996) Survey of Non-xanthine Derivatives as Adenosine Receptor Ligands. Nucleosides, Nucleotides 15: 693-718.
Slominski et al., (2004) Melanin pigmentation in mammalian skin and its hormonal regulation. Physiol Rev 84(4): 1155-1228.
Sodeoka et al., (2001) Synthesis of a tetronic acid library focused on inhibitors of tyrosine and dual-specificity protein phosphatases and its evaluation regarding VHR and CDC25B inhibition. J Med Chem 44: 3216-22.
Tchilibon et al., (2005) (N)-methanocarba 2,N6-disubstituted adenine nucleosides as highly potent and selective A3 adenosine receptor agonists. J Med Chem 48(6): 1745-58.
van Rhee et al., (1996) Development of 1,4-Dihydropyridines as Selective A3 Adenosine Receptors Antagonists. Drug Devel Res 37: 131.
van Rhee et al., (1996) Interaction of 1,4-dihydropyridine and pyridine-derivatives with adenosine receptors: selectivity for A3 receptors. J Med Chem 39: 2980-9.
van Rhee et al., (1996) Tetrahydrobenzothiophenone Derivatives as a Novel Class of Adenosine Receptor Antagonists. J Med Chem 39: 398-406.
von Lubitz (1999) Adenosine and cerebral ischemia: therapeutic future or death of a brave concept? Eur J Pharmacol 371(1): 85-102.
Yao et al., (1997) Adenosine A3 receptor agonists protect HL-60 and U-937 cells from apoptosis induced by A3 antagonists. Biochem Biophys Res Comm 232(2): 317-322.

* cited by examiner

A3 ADENOSINE RECEPTOR LIGANDS FOR MODULATION OF PIGMENTATION

CROSS REFERENCE TO RELATED APPLICATIONS

The present application is a divisional of U.S. patent application Ser. No. 13/386,339, filed on Jan. 20, 2012, which is a 35 U.S.C. §371 National Phase Entry application from PCT/IL2010/000576, filed Jul. 20, 2010, and designating the United States, which claims the benefit of priority under 35 USC 119(e) of U.S. Provisional Patent Application No. 61/227,079, filed Jul. 21, 2009, the contents of which are incorporated herein by reference in their entireties.

FIELD OF THE INVENTION

The present invention relates to pharmaceutical and cosmetic compositions comprising A3 adenosine receptor ligands and methods of use thereof for modulating melanin production, secretion and/or accumulation in skin.

BACKGROUND OF THE INVENTION

A variety of dermatological compositions have been suggested for skin whitening to counteract abnormal pigmentation occurring in various disorders. Such disorders include post inflammatory hyperpigmentation, (attributed to various preceding conditions such as infections, allergic reactions, mechanical injuries, reactions to medications, phototoxic eruptions, trauma for example burns, and inflammatory diseases such as lichen planus, lupus erythematosus, atopic dermatitis), melasma, periorbital darkening, pigmented keratosis, lentigo senilis, ephelides, chloasma, café au lait spots, liver spots, freckles and lesions observed in Addison's disease, hemochomatosis, piebaldism, and the like. In addition, there is an enormous demand within populations with genetically inherited dark skin to lighten their skin color.

In mammals, skin and hair color is primarily determined by the amount of melanin pigments that are synthesized by melanocytes within specialized organelles called melanosomes. There is no evidence for differences in melanosome biogenesis between follicular and epidermal melanocytes. Thus, in black hair follicles, melanocytes contain the largest number and most electron-dense melanosomes. In brown hair, bulb melanocytes are smaller, and in blonde hair melanosomes are poorly melanized (Slominski et al., 2004). Melanin synthesis (also termed melanogenesis) is controlled by at least three enzymes: tyrosinase, tyrosinase-related-protein 1 (TRP1) and tyrosinase-related-protein 2 (TRP2), among which tyrosinase has the key role of catalyzing the rate limiting steps of the hydroxylation reaction of tyrosine to L-DOPA and the oxidation reaction of L-DOPA into dopaquinone.

Melanogenesis and melanosome transfer from the melanocytes to the neighboring keratinocytes involve a complex network of regulatory processes, and are induced primarily by ultraviolet radiation. Solar radiation acts either directly on melanocytes or indirectly though the release of keratinocyte-derived melanocyte stimulating hormone (α-MSH), a potent inducer of melanogenesis both in vivo and in vitro (Englaro et al., 1998). α-MSH stimulates adenylate cyclase activity leading to an increase in cAMP level which elevates the expression of melanogenic enzymes, in particular that of tyrosinase (Hunt et al., 1994; Im et al., 1998; Lee et al., 2007). In contrast, inhibition of adenylate cyclase activity resulting in decreased levels of intracellular cAMP is associated with inhibition of melanogenesis and depigmentation (Choi et al., 2008; Lee et al., 2007). Keratinocyte growth factor (KGF), a paracrine mediator of human keratinocyte growth and differentiation, has been shown to induce melanosome transfer from melanocytes to keratinocytes through a phagocytic process (Cardinali et al., 2005).

Dermatological compositions which have been disclosed for hair and skin bleaching typically act by destroying or disrupting melanin granules, inhibiting melanin formation (such as by inhibiting tyrosinase or melanocyte activity), or both. Various skin whitening compositions are disclosed for example, in U.S. Pat. Nos. 5,980,904, 5,747,006, and 6,077,503. Many of these compositions contain harsh chemicals such as peroxides, acids or formaldehyde, or thiolated compounds such as glutathione, cysteine, mercaptosuccinic acid, mercaptodextran, and mercaptoethanol, which have an objectionable odor that makes products containing them undesirable for use.

Hydroquinone for topical application is approved in the United States for non-prescription use, and acts by suppressing melanocyte activity. U.S. Pat. No. 6,068,834 discloses hydroquinone-based compounds and compositions Hydroquinone, however, is oxidized by air, light, and tyrosinase itself, which adversely affects the shelf life of preparations containing it and its bioavailability upon application. Hydroquinone can cause burning, redness, sensitization and irritation in some individuals, particularly after application of quantities sufficient to cause skin bleaching. Oxidized products of hydroquinone have also been implicated in skin irritation and pigmentation rebound.

Retinoids and corticosteroids for topical use have been suggested as hypopigmenting agents, as have laser treatment and chemical peels, but these fall short of desirable responses. A combination therapy containing tretinoin and fluocinolone with hydroquinone has been disclosed (Willis, 2000). Kojic acid and arbutin have also been suggested (Draelos, 2007), but these weak tyrosinase inhibitors generally display low bioavailability. Furthermore, arbutin is ineffective at levels allowed by Japanese quasi-drug regulations, and kojic acid has been banned for quasi-drug usage in Japan due to its mutagenic properties (Boissy et al., 2005).

U.S. Pat. No. 7,019,029 discloses the use of hydroxythronic acid derivatives alone or in combination with tetronic acid, hydroquinone, glycolic acid and/or ascorbyl palmitate as skin whiteners.

Various plant extracts have been disclosed for bleaching skin or for enhancing the appearance of fair skin, which have in some cases been used for centuries in Asia or Europe. U.S. Pat. No. 5,602,259 discloses a furanone extracted from Pinaceae plants for use in whitening skin by inhibiting melanin formation.

U.S. Pat. No. 5,905,091 discloses a composition comprising a carrier and a prostaglandin, and optionally comprising a lysosomotropic agent, a phosphodiesterase inhibitor, and/or methylxanthines, and a method of use thereof for stimulating synthesis of melanin in a human melanocyte thereby enhancing pigmentation of human skin.

U.S. Pat. No. 5,554,359 discloses a composition comprising a lysosomotropic agent, and optionally phosphodiesterase inhibitors, and/or methylxanthines for increasing synthesis of melanin in a human melanocyte thereby enhancing pigmentation of human skin.

Adenosine is an endogenous purine nucleoside ubiquitous in mammalian cells, which is an important regulatory compound that mediates many physiological effects via binding to its specific A1, A2 and A3 cell surface receptors. Interaction of adenosine with its receptors initiates signal transduction pathways, in particular that of the adenylate cyclase effector system, which utilizes cAMP as a second messenger. The A1 and A3 adenosine receptors, which are coupled to Gi proteins, inhibit adenylate cyclase and lead to a decrease in the level of intracellular cAMP, while the A2 adenosine receptor, which is coupled to Gs proteins, activates adenylate cyclase, thereby increasing cAMP levels (see for example, Fredholm et al., 2000).

The use of various adenosine receptor agonists and antagonists for treatment of different disease states and pathologies has been suggested, including for example, inflammation (Salvatore et al., 2000), neurodegeneration (Von Lubitz, 1999), asthma (Forsythe and Ennis, 1999), cardiac ischemia (Liang and Jacobson, 1998), and tumors (Yao et al., 1997).

U.S. Pat. No. 7,064,112 discloses the use of A3 adenosine receptor agonists for the prevention and treatment of leukopenia, and for the inhibition of abnormal cell growth and proliferation of tumor cells.

WO 2008/023362 discloses methods and compositions useful for treating cancer based on the combination of methotrexate and an A3 adenosine receptor agonist.

U.S. Pat. No. 7,465,715 discloses the use of A3 adenosine receptor agonists for the treatment of multiple sclerosis.

U.S. Pat. No. 7,465,715 discloses the use of A3 adenosine receptor agonists for inhibiting viral replication in cells.

U.S. Pat. No. 7,141,553 discloses the use of A3 adenosine receptor agonists for the treatment of inflammatory arthritis.

U.S. Pat. No. 5,998,423 discloses the use of adenosine A1 receptor antagonists and of adenosine A2 receptor agonists for increasing melanin production in skin or hair, and the use of adenosine A1 receptor agonists and adenosine A2 receptor antagonists for decreasing melanin production in skin or hair.

U.S. Patent Application Publication No. 2002/0115635 discloses a treatment method comprising administering to a subject an active agent selected from the group consisting of an adenosine A1 receptor ligand, an A2 adenosine receptor ligand, an adenosine A3 receptor ligand and a combination thereof. The method is disclosed to be effective for a variety of diseases and disorders, inter alia hair loss, which require elevation of GSK-3β activity for treatment.

U.S. Patent Application Publication No. 2007/0299032 discloses a method for maintaining and promoting hair thickening comprising applying to the scalp an external skin preparation containing one or more types of agents, inter alia the A3 adenosine receptor agonist C1-IB-MECA.

U.S. Patent Application Publication No. 2008/0044439 discloses use of p38 inhibitors for treating skin conditions such as vitiligo, and describes adenosine A3 antagonists as possible p38 inhibitors.

There remains an unmet need for new compositions which modulate melanin production and thereby lighten the skin or hair or promote pigmentation for both pharmaceutical and cosmetic purposes.

SUMMARY OF THE INVENTION

The present invention provides methods as well as pharmaceutical and cosmetic compositions useful for modulating the production, secretion and/or accumulation of melanin in skin, in particular within skin cells such as melanocytes and keratinocytes, thereby modulating pigmentation of the skin and hair. In particular, the present invention provides use of A3 adenosine receptor antagonists in compositions and methods for the treatment and amelioration of hyper-pigmentation skin conditions and for cosmetic lightening of skin and hair color, as well as use of A3 adenosine receptor agonists in compositions and methods for the treatment and amelioration of hypo-pigmentation skin conditions and for cosmetic skin tanning.

The present invention is based in part on the surprising discovery that activation of the A3 adenosine receptor causes an increase in pigmentation, while deactivation of the A3 adenosine receptor causes a decrease in pigmentation. The present invention is highly unexpected over the prior art, which teaches that activation of the A3 adenosine receptor, which is known to be negatively coupled to adenylate cyclase, should inhibit melanogenesis due to decreased intracellular levels of cAMP and thus lead to depigmentation.

Surprisingly and in contrast to the teachings of the prior art, the inventors of the present invention have shown that melanocytes treated with the A3 adenosine receptor agonist IB-MECA unexpectedly exhibit an increase in pigmentation, attributable to an increase in melanin secretion by the melanocytes. Similarly, the inventors of the present invention have shown that treatment of melanoctyes with the A3 adenosine receptor antagonist MRS-1523, unexpectedly led to depigmentation.

Moreover, the inventors of the present invention have found that A3 adenosine receptor ligands may exert modulation of pigmentation by altering melanin production and/or secretion in melanocytes, as well as altering melanin accumulation in keratinocytes and/or melanin secretion from melanocytes to keratinocytes.

Without wishing to be bound by any theory or mechanism of action, it is contemplated that the effect of A3 adenosine receptor agonists in enhancing pigmentation and the effect of A3 adenosine receptor antagonists in decreasing pigmentation, may respectively involve Mitf activation and Mitf downregulation, and mediation thereof via the Akt and ERK signaling pathways.

According to a first aspect, the present invention provides a method for modulating melanin production, secretion, accumulation or a combination thereof in at least one skin cell, comprising the step of contacting the skin cell with a compound selected from the group consisting of an A3 adenosine receptor antagonist and an A3 adenosine receptor agonist in an amount effective to modulate melanin production, secretion, and/or accumulation in the skin cell.

In particular embodiments, the at least one skin cell is a melanocyte, a keratinocyte, or tissue comprising a plurality of melanocytes and/or keratinocytes.

In a particular embodiment, the compound is an A3 adenosine receptor agonist, and the modulating comprises increasing at least one of melanin production, secretion or accumulation. Each possibility represents a separate embodiment of the invention.

In a particular embodiment, the skin cell is a melanocyte, and the A3 adenosine receptor agonist is in an amount effective to increase at least one of melanin production and melanin secretion in said melanocyte. Each possibility represents a separate embodiment of the invention.

In a particular embodiment, the skin cell is a keratinocyte, and the A3 adenosine receptor agonist is in an amount effective to increase accumulation of melanin in said keratinocyte. In a particular embodiment, the A3 adenosine receptor agonist is in an amount effective to increase secretion of melanin from a melanocyte to a keratinocyte.

According to particular embodiments, the A3 adenosine receptor agonist has a binding affinity (Ki) for the A3 adenosine receptor that is less than about 200 nM, preferably less than about 100 nM, more preferably less than about 50 nM, even more preferably less than about 10 nM. Each possibility represents a separate embodiment of the invention. According to particular embodiments, the binding affinity of the A3 adenosine receptor agonist for the adenosine A3 receptor is at least 20 times greater than the binding affinity of said agonist for the A1 adenosine receptor.

According to particular embodiments, the A3 adenosine receptor is the human A3 adenosine receptor.

According to particular embodiments, the A3 adenosine receptor agonist is a selective A3 adenosine receptor agonist.

According to particular embodiments of the invention disclosed herein, the A3 adenosine receptor agonist is an $N^6$-substituted-adenosine-5'-uronamide. In some embodiments, the $N^6$-substituted-adenosine-5'-uronamide is selected from the group consisting of an $N^6$-monosubstituted-adenosine-5'-uronamide and an $N^6$-disubstituted-adenosine-5'-uronamide. According to particular embodiments, the A3 adenosine receptor agonist is selected from the group consisting of an $N^6$-benzyladenosine-5'-uronamide; an $N^6$-4-substituted-sulfonamidophenylcarbamoyl-adenosine-5'-uronamide; a 2-chloro-$N^6$-substituted-4'-thioadenosine-5 '-uronamide; an (N)-methanocarba adenosine-5'-uronamide and derivatives and analogs thereof. Each possibility represents a separate embodiment of the present invention.

According to particular embodiments, the A3 adenosine receptor agonist is selected from the group consisting of $N^6$-(3-iodobenzyl) adenosine-5'-(N-methyluronamide) (IB-MECA); 2-chloro-$N^6$-(3-iodobenzyl)-adenosine-5'-(N-methyluronamide) (C1-IB-MECA); $N^6$-(4-amino-3-iodobenzyl)-adenosine-5'-(N-methyluronamide) (AB-MECA); $N^6$-2-(4-aminophenyl)ethyladenosine (APNEA); 2-(1-hexynyl)-N-methyladenosine, 2-chloro-$N^6$-(3-iodobenzyl)-9-[5-(methylcarbamoyl)-D-ribofuranosyl]adenine (CF-102); (2S,3S,4R,5R)-3-amino-5-[6-(2,5-dichlorobenzylamino)purin-9-yl]-4-hydroxytetrahydrofuran-2-carboxylic acid methylamide (CP-532,903); 2-chloro-4'-thioadenosine-5'-methyluronamide; (1'R,2'R,3'S,4'R,5'S)-4-{2-chloro-6-[(3-chlorophenylmethyl)amino]purin-9-yl}-1-(methylaminocarbonyl)bicyclo[3.1.0]hexane-2,3-diol (MRS-3558), and derivatives and analogs thereof. Each possibility represents a separate embodiment of the present invention.

In a particular embodiment, the A3 adenosine receptor agonist is selected from the group consisting of $N^6$-(3-iodobenzyl) adenosine-5'-(N-methyluronamide) (IB-MECA); 2-chloro-$N^6$-(3-iodobenzyl)-adenosine-5'-(N-methyluronamide) (C1-IB-MECA); $N^6$-(4-amino-3-iodobenzyl)-adenosine-5'-(N-methyluronamide) (AB-MECA); and $N^6$-2-(4-aminophenyl)ethyladenosine (APNEA).

In a particular embodiment, the A3 adenosine receptor agonist is selected from the group consisting of $N^6$-(3-iodobenzyl) adenosine-5'-(N-methyluronamide) (IB-MECA); 2-chloro-$N^6$-(3-iodobenzyl)-adenosine-5'-(N-methyluronamide) (C1-IB-MECA); 2-(1-hexynylhexynyl)-N-methyladenosine; 2-chloro-$N^6$-(3-iodobenzyl)-9-[5-(methylcarbamoyl)-D-ribofuranosyl]adenine (CF-102); and (2S,3S,4R,5R)-3-amino-5-[6-(2,5-dichlorobenzylamino)purin-9-yl]-4-hydroxytetrahydrofuran-2-carboxylic acid methyl amide (CP-532,903).

In a particular embodiment, the A3 adenosine receptor agonist is selected from the group consisting of $N^6$-(3-iodobenzyl) adenosine-5'-(N-methyluronamide) (IB-MECA) and 2-chloro-$N^6$-(3-iodobenzyl)-adenosine-5'-(N-methyluronamide) (C1-IB-MECA).

According to a currently preferred embodiment, the A3 adenosine receptor agonist is $N^6$-(3-iodobenzyl) adenosine-5'-(N-methyluronamide) (IB-MECA).

According to another embodiment, the method for increasing at least one of melanin production, secretion or accumulation further comprises contacting the skin cell with an allosteric modulator of the A3 adenosine receptor. In particular embodiments, the allosteric modulator is an allosteric enhancer of the A3 adenosine receptor.

In a particular embodiment, the skin cell is in a human subject having a hypo-pigmentation disorder selected from the group consisting of vitiligo, piebaldism, leukoderma due to cicatrisation, nevus depigmentosis and depigmentation due to a skin graft procedure.

According to another particular embodiment of the method disclosed herein, the compound is an A3 adenosine receptor antagonist, and the modulating comprises decreasing at least one of melanin production, secretion or accumulation in the skin cell. Each possibility represents a separate embodiment of the invention.

According to a particular embodiment, the skin cell is a melanocyte, and the A3 adenosine receptor antagonist is in an amount effective to decrease at least one of melanin production and melanin secretion in said melanocyte. Each possibility represents a separate embodiment of the invention.

According to a particular embodiment, the skin cell is a keratinocyte, and the A3 adenosine receptor antagonist is in an amount effective to decrease accumulation of melanin in said keratinocyte. According to a particular embodiment, the A3 adenosine receptor antagonist is in an amount effective to decrease secretion of melanin from a melanocyte to a keratinocyte.

According to particular embodiments, the A3 adenosine receptor antagonist has a binding affinity (Ki) for the A3 adenosine receptor that is less than about 200 nM, preferably less than about 100 nM, more preferably less than about 50 nM, even more preferably less than 10 nM. Each possibility represents a separate embodiment of the invention.

According to particular embodiments, the binding affinity of the A3 adenosine receptor antagonist for the adenosine A3 receptor is at least 20 times greater than the binding affinity of said antagonist for the A1 adenosine receptor.

According to particular embodiments, the A3 adenosine receptor is the human A3 adenosine receptor. According to some embodiments, the A3 adenosine receptor antagonist is a selective A3 adenosine receptor antagonist.

According to a particular embodiment, the A3 adenosine receptor antagonist is a compound selected from the group consisting of a dihydropyridine, a pyridine, a pyridinium salt, a triazoloquinazoline, an imidazoquinoline, a triazolopurine, an $N^6$-substituted-7-deazapurine, and derivatives and analogs thereof. Each possibility represents a separate embodiment of the present invention.

According to particular embodiments, the A3 adenosine receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl]ester (MRS-1334); 3-ethyl-5-benzyl-2-methyl-4-phenylethynyl-6-phenyl-1,4-(±)-dihydropyridine-3,5 dicarboxylate (MRS-1191); 3-ethyl 5-benzyl-2-methyl-6-phenyl-4-styryl-1,4-(±)-dihydropyridine-3,5-dicarboxylate (MRS-1097); 5-n-butyl-8-(4-trifluoromethylphenyl)-3H-[1,2,4]triazolo-[5,1-i]purine OT-7999; (2R,3R,4S,5S)-2-[$N^6$-3-iodobenzyl)adenos-9'-yl]-7-aza-1-oxa-6-oxospiro[4,4]-nonan-4,5-diol (MRS-1292); N-(2- methoxyphenyl)-N'-[2-(3-pyridinyl)-4-quinazolinyl]-urea (VUF-5574); (8R)-8-ethyl-1,4,7,8-tetrahydro-4-5H-imidazo[2,1-i]purin-5-one (PSB-11); 2-phenoxy-6-(cyclohexylamino)purine (MRS-3777); 5N-(4-methoxyphenylcarbamoyl)amino-8-propyl-2-(2-furyl)pyrazolo[4,3-e]-1,2,4-triazolo[1,5-c]pyrimidine (MRE3008F20) and derivatives and analogs thereof. Each possibility represents a separate embodiment of the present invention.

In a particular embodiment, the A3 adenosine receptor antagonist is selected from the group consisting of 3-propyl-6-ethyl-5 [(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl]ester (MRS-1334); and 3-ethyl-5-benzyl-2-methyl-4-phenylethynyl-6-phenyl-1,4-(±)-dihydropyridine-3,5 dicarboxylate (MRS-1191).

According to a currently preferred embodiment, the A3 adenosine receptor antagonist is 3-propyl-6-ethyl-5 [(ethylthio)carbonyl]-2-phenyl-4-propyl-3-pyridine carboxylate (MRS-1523).

According to particular embodiments of the method for decreasing at least one of melanin production, secretion or accumulation, the method further comprises the step of contacting the skin cell with at least one of hydroxytetronic acid; tetronic acid; hydroquinone; an α-hydroxy acid, a fatty acid ester of ascorbic acid; a tyrosinase inhibitor and a tyrosine phosphatase inhibitor.

In a particular embodiment, the skin cell is in a human subject having a hyper-pigmentation disorder selected from the group consisting of pigmented spots, lentigo senilis, freckles, café au lait spots, liver spots, ephelides, periorbital darkening, post-inflammatory hyper-pigmentation, pigmented keratosis, melasma, chloasma, and hyper-pigmentation due to a skin graft procedure.

In another aspect, the invention further provides a compound selected from the group consisting of an A3 adenosine receptor antagonist and an A3 adenosine receptor agonist for use in modulating melanin production, secretion, accumulation or a combination thereof in at least one skin cell.

In a particular embodiment, the compound is an A3 adenosine receptor agonist in an amount effective for increasing at least one of melanin production, secretion or accumulation. In another particular embodiment, the compound is an A3 adenosine receptor antagonist in an amount effective for decreasing at least one of melanin production, secretion or accumulation. Each possibility represents a separate embodiment of the invention.

According to another aspect, the present invention provides a cosmetic or pharmaceutical composition for use in modulating at least one of melanin production, secretion or accumulation in skin, wherein the composition comprises as an active ingredient an A3 adenosine receptor antagonist or an A3 adenosine receptor agonist; and a pharmaceutically acceptable carrier. In a particular embodiment the pharmaceutically acceptable carrier is capable of delivering the active ingredient to a skin cell under in vivo conditions.

According to one embodiment, the composition comprises an A3 adenosine receptor agonist as described herein, in an amount effective for increasing at least one of melanin production, secretion or accumulation in skin. Each possibility represents a separate embodiment of the invention.

According to a particular embodiment, the composition comprises an A3 adenosine receptor agonist in an amount effective for increasing at least one of melanin production and melanin secretion in a melanocyte. Each possibility represents a separate embodiment of the invention.

According to a particular embodiment, the composition comprises an A3 adenosine receptor agonist in an amount effective for increasing melanin accumulation in a keratinocyte. According to a particular embodiment, the composition comprises an A3 adenosine receptor agonist in an amount effective for increasing melanin secretion from a melanocyte to a keratinocyte.

According to a particular embodiment, the composition comprises $N^6$-(3-iodobenzyl) adenosine-5'-(N-methyluronamide) (IB-MECA) as the A3 adenosine receptor agonist.

According to another embodiment, the composition comprising an A3 adenosine receptor agonist, further comprises an allosteric enhancer of the A3 adenosine receptor.

According to another embodiment, the composition comprises an A3 adenosine receptor antagonist as described herein, in an amount effective for decreasing at least one of melanin production, secretion or accumulation in skin. Each possibility represents a separate embodiment of the invention.

According to a particular embodiment, the composition comprises an A3 adenosine receptor antagonist in an amount effective for decreasing at least one of melanin production and melanin secretion in a melanocyte. Each possibility represents a separate embodiment of the invention.

According to a particular embodiment, the composition comprises an A3 adenosine receptor antagonist in an amount effective for decreasing melanin accumulation in a keratinocyte. According to a particular embodiment, the composition comprises an A3 adenosine receptor antagonist in an amount effective for decreasing melanin secretion from a melanocyte to a keratinocyte.

According to a particular embodiment, the composition comprises 3-propyl-6-ethyl-5[(ethylthio)carbonyl]-2-phenyl-4-propyl-3-pyridine carboxylate (MRS-1523) as the A3 adenosine receptor antagonist.

According to another embodiment, the composition comprising an A3 adenosine receptor antagonist further comprises at least one of hydroxytetronic acid; tetronic acid; hydroquinone; an α-hydroxy acid, a fatty acid ester of ascorbic acid; a tyrosinase inhibitor and a tyrosine phosphatase inhibitor.

According to particular embodiments, the compositions are formulated for administration by a route selected from the group consisting of direct administration into, onto or in the vicinity of a skin site of hyper-pigmented or hypo-pigmented tissue, topical, intradermal, transdermal, subcutaneous, intramuscular, intraperitoneal, intravenous, subcutaneous, intranasal and oral administration.

According to another aspect, the present invention provides a method for treating or ameliorating a hyper-pigmentation condition of human skin, the method comprising administering to a human subject in need thereof an effective amount of a cosmetic or pharmaceutical composition comprising as an active ingredient an A3 adenosine receptor antagonist according to the principles of the invention.

According to particular embodiments, the hyper-pigmentation condition is selected from the group consisting of pigmented spots, lentigo senilis, freckles, café au lait spots, liver spots, ephelides, periorbital darkening, post-inflammatory hyper-pigmentation, pigmented keratosis, melasma, chloasma and hyper-pigmentation due to a skin graft procedure. In a particular embodiment the composition is a cosmetic composition for lightening dark skin.

According to another aspect, there is provided a cosmetic or pharmaceutical composition comprising an A3 adenosine receptor antagonist for use in treating or ameliorating a hyper-pigmentation condition of human skin, in accordance with the invention.

According to yet another aspect, the present invention provides a method for treating or ameliorating a hypo-pigmentation condition of human skin comprising administrating to a human subject in need thereof an effective amount of a cosmetic or pharmaceutical composition comprising as an active ingredient an A3 adenosine receptor agonist according to the principles of the invention. According to particular embodiments, the hypo-pigmentation condition is selected from the group consisting of pigmented vitiligo, piebaldism, leukoderma due to cicatrisation, nevus depigmentosis, and depigmentation due to a skin graft procedure. In a particular embodiment the composition is a cosmetic composition for tanning fair skin.

In particular embodiments, the administering comprises topically applying the composition comprising the A3 adenosine receptor agonist or the A3 adenosine receptor antagonist to skin of the subject. In particular embodiments, the A3 adenosine receptor agonist or the A3 adenosine receptor antagonist is topically administered over a period of at least two weeks, or at least one month, or at least two months.

According to another aspect, there is provided a cosmetic or pharmaceutical composition comprising an A3 adenosine receptor agonist for use in treating or ameliorating a hypo-pigmentation condition of human skin, in accordance with the invention.

According to additional embodiments, the administering of the cosmetic or pharmaceutical composition to the subject is carried out by a route selected from the group consisting of direct administration into, onto or in the vicinity of hyper-pigmented or hypo-pigmented skin, topical, intradermal, transdermal, subcutaneous, intramuscular, intraperitoneal, intravenous, subcutaneous, intranasal and oral administration. According to certain preferred embodiments, the composition is topically administered.

According to further embodiments, the cosmetic or pharmaceutical composition is in a form selected from the group consisting of a solution, a suspension, an emulsion, a cream, a gel, an aerosol formulation and a sustained-release formulation.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A shows melanin levels in cell lysates and in the media expressed as μg melanin/mg protein.

FIG. 1B shows total melanin levels expressed as percent of control. Each value is expressed as the mean±SD, n=3 *p<0.05, **p<0.001 compared to the control.

FIG. 1C is a photograph showing the dose response of melanin secretion to the media by cells treated with the indicated concentrations of IB-MECA.

FIG. 2A shows melanin levels in cell lysates and in the media expressed as μg melanin/mg protein.

FIG. 2B shows total melanin levels expressed as percent of control. Each value is expressed as the mean±SD, n=3 *p<0.05, **p<0.001 compared to the control.

FIG. 3A is a photograph of the cells following treatment with the indicated compounds for 24 h. Arrows indicate positions of melanosomes. N, nucleus.

FIG. 3B depicts transfer of melanosomes from one melanocyte to the other by a dendrite-dendrite interaction. Arrow indicates position of melanosomes.

FIG. 3C shows total melanin levels after various treatment intervals expressed as percent of control.

FIG. 3D shows melanin levels expressed as μg melanin/mg protein in cell lysates and in the media following exposure of melanocytes to IB-MECA or MRS-1523 for 5-days. For FIGS. 3C and 3D, each value is expressed as the mean±SD, n=3 *p<0.05, **p<0.001 compared to the control.

FIG. 3E is a photograph showing melanin secretion to the media following 5 days of exposure to IB-MECA or MRS-1523, as indicated.

FIG. 4A shows melanin levels in cell lysates and in the media expressed as μg melanin/mg protein.

FIG. 4B shows total melanin expressed as percent of control. Each value is expressed as the mean±SD, n=3 *p<0.05, **p<0.001 compared to the control.

FIG. 5A shows western blot analysis of cell protein extracts (20 μg/lane) analyzed for Akt phosphorylation compared to total Akt expression. Time intervals of exposure to the ligands are indicated.

FIG. 5B shows confocal image analysis of B16 melanocytes exposed to the indicated ligands for 3 h, following labeling with anti-phospho-Akt antibody and Cy3-conjugated donkey anti-rabbit antibody, and counter staining with DAPI. Arrow indicates phospho-Akt. Scale bars correspond to 25μ.

FIG. 6A shows analysis of proteins from cells exposed to the indicated ligands for 10 min, 30 min or 3 h.

FIG. 6B shows analysis of proteins from cells exposed to the indicated ligands for 72 h.

FIG. 8A is a photograph of skin samples following treatment with the indicated compounds after 12 days of culture.

FIG. 8B shows light microscope images (×400) of epidermis peeled from skin samples treated with IB-MECA or MRS-1523 (10 μM each) or hydroquinone (100 μM) as indicated, stained with DOPA and mounted on slides. FIG. 8D shows light microscope images (×400) of epidermis peeled from skin samples treated with IB-MECA or MRS-1523 (50 μM each) or hydroquinone (100 μM) as indicated, stained with DOPA and mounted on slides.

FIGS. 8C and 8E show the degree of pigmentation (density) in the samples shown in FIGS. 8B and 8D respectively, as evaluated by measurement of the light transmission capacity though the peeled epidermis sheets using single channel transmission by light microscopy (×50). D-P-M, DOPA-positive melanoctyes.

DETAILED DESCRIPTION OF THE INVENTION

Figure 1A:
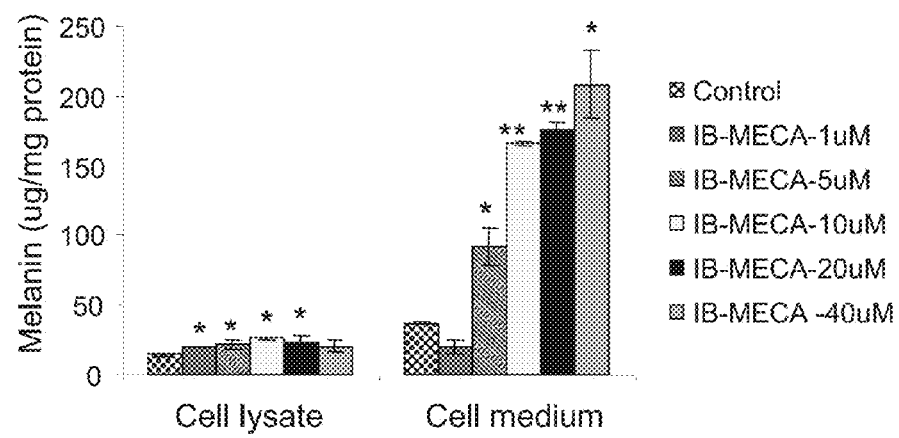
FIGS. 1A-1C show the effect of the A3 adenosine receptor agonist IB-MECA on melanin synthesis and secretion in B16 melanocytes. Cells were cultured in 10% DMEM in the presence of various concentrations of IB-MECA for 5 days. Levels of melanin in the media and in the cell lysates, and total protein content in the cell lysates were then determined as described in Materials and Methods. Melanin levels were measured and calculated separately for each sample.

The present invention provides methods as well as pharmaceutical and cosmetic compositions useful for modulating i.e. increasing or decreasing, the production, secretion and/or accumulation of melanin in skin cells, thereby enabling alteration of pigmentation of the skin and hair. In particular, the present invention provides methods and compositions comprising use of A3 adenosine receptor agonists for enhancing the tanning process by increasing skin pigmentation, as well as methods and compositions comprising use of A3 adenosine receptor antagonists for reducing skin pigmentation to lighten the skin color.

The inventors of the present invention have surprisingly found that A3 adenosine receptor agonists, such as IB-MECA, cause an increase in melanin synthesis in melanocytes in a dose-dependent fashion, as shown in Example 1. Furthermore, A3 adenosine receptor agonists cause a significant increase in melanin secretion from the cells, as shown in Example 3. In addition, agonist treatment further exerts the effect of altering accumulation and/or re-distribution of melanosomes within the cell, as shown in Example 3, and moreover may promote melanosome transfer from melanocytes to keratinoctyes, as shown in Example 9. Example 3 further shows that the increase in melanin production occurs in a time-dependent fashion, indicating that the invention may be effectively used for gradually increasing skin pigmentation, which is advantageous both for cosmetic applications directed at achieving "tanning" effects over a period of time, and for pharmaceutical applications directed at ameliorating hypo-pigmentation skin disorders.

The principles of the invention directed to augmenting skin pigmentation have further been demonstrated in ex vivo studies of skin explants as shown in Examples 8 and 9, which provide confirmation of the increase in melanin production and/or secretion in melanocytes and/or melanin accumulation in keratinocytes using a number of histological and microscopic methods.

Alternatively, it is now disclosed that A3 adenosine receptor antagonists, such as MRS-1523, cause a decrease in melanin synthesis in melanocytes in a dose dependent fashion, as shown in Example 2. This reduction also occurs in a time-dependent fashion, as shown in Example 3. The principles of the invention directed to reducing skin pigmentation have further been demonstrated in ex vivo studies of skin explants as shown in Examples 8 and 9, which provide confirmation of the decrease in melanin production and/or secretion in melanocytes and/or melanin accumulation in keratinocytes using a number of histological and microscopic methods.

Examples 5 to 7 suggest that the effect of A3 adenosine receptor agonists in enhancing pigmentation, and the effect of A3 adenosine receptor antagonists in decreasing pigmentation, may involve Mitf activation and Mitf downregulation respectively, mediation of which occurs via the Akt and ERK signaling pathways.

Definitions

As used herein, the term "ligand of the A3 adenosine receptor" refers to a compound which specifically binds the A3 adenosine receptor and thereby causes either activation of the A3 adenosine receptor (i.e., A3 adenosine receptor agonist), or inhibition of the A3 adenosine receptor (i.e., A3 adenosine receptor antagonist).

As used herein, the term "A3 adenosine receptor agonist" refers to a ligand of the A3 adenosine receptor, which upon binding to the receptor exerts full or partial activation of that receptor.

As used herein, the term "A3 adenosine receptor antagonist" refers to a ligand of the A3 adenosine receptor, which upon binding to the receptor exerts full or partial inhibition of that receptor.

As used herein, the term "selective" means that the binding affinity of an A3 adenosine receptor agonist or of an A3 adenosine receptor antagonist to the A3 adenosine receptor is at least 20 fold, preferably at least 50 fold and more preferably at least 100 fold greater than the binding of the same compound to a heterologous adenosine receptor, for example the A1 adenosine receptor, the A2a adenosine receptor or the A2b adenosine receptor of the same species, or the A3 adenosine receptor of a different species.

As used herein, the term "allosteric enhancer of the A3 adenosine receptor" refers to a compound which enhances the binding of an A3 adenosine receptor agonist to the A3 adenosine receptor, thereby increasing the activation effect of the agonist.

As used herein, the term "modulating melanin production" means affecting a change in the pattern of melanin production, for example increasing or decreasing the overall amount of melanin produced by a cell, or increasing or decreasing the rate of melanin production by a cell.

As used herein, the term "modulating melanin secretion" means affecting a change in the pattern of melanin secreted from a cell, for example increasing or decreasing the overall amount of melanin secreted from a cell, or increasing or decreasing the rate of melanin secreted from a cell. The term also encompasses an alteration in the target destination of melanin secretion such as into the extracellular medium or space, or into a different cell or into a different cell type.

As used herein, the term "modulating melanin accumulation" means affecting a change in the pattern of melanin deposition or sequestration in or among cell compartments or organelles, or among cell types.

As used herein, the term "skin cell" refers to any type of skin cell, including skin cells involved in melanin production and/or accumulation such as melanocytes and keratinocytes, and precursors thereof.

As used herein, the term "at least one skin cell" encompasses both a single skin cell and a plurality of skin cells, including those forming skin tissue and skin surface areas of any size or dimension, for example as measured in square meters of body surface area.

A3 Adenosine Receptor Agonists

As used herein, an A3 adenosine receptor agonist (also referred to herein as "A3RAg") is any compound capable of specifically binding to the A3 adenosine receptor (also referred to herein as "A3R"), and capable of fully or partially activating said receptor. The A3RAg is thus a compound that exerts its prime effect though the binding and activation of the A3R. The ability of a compound to bind A3R may be assessed in a competitive binding assay, typically in which a test compound is assessed for the ability to displace a radiolabeled form of a known A3RAg (for example [125I]-AB-MECA) from binding to the A3R present on cells or membranes. Such binding assays are described for example in Olah et al., Mol Pharmacol. 1994 May; 45(5):978-82; Auchambach et al. Mol Pharmacol. 1997 November; 52(5):846-60; and Kreckler et al., J Pharmacol Exp Ther. 2006 April; 317(1):172-80. The ability of a compound to activate A3R may also be assessed in a functional assay based on determination of downstream signaling events, in particular the effect on adenylyl cyclase as measured by the effect (i.e. increase or decrease) on cAMP level. Such cAMP assays used to assess A3R activation by various compounds are described for example in Wan et al., J Pharmacol Exp Ther. 2008 January; 324(1): 234-43 and Auchambach et al. Mol Pharmacol. 1997 November; 52(5):846-60.

The affinity of an A3RAg to the human A3R as well as its relative affinity to the other human adenosine receptors (A1, A2a and A2b) can be determined by binding assays and cAMP assays, as described above. In preferred embodiments, the A3RAg is a selective A3RAg, meaning that its binding affinity for the A3 adenosine receptor is greater than the binding affinity of the same compound for a different adenosine receptor, for example the A1 adenosine receptor. In some preferred embodiments, the binding affinity of the A3RAg for the A3 adenosine receptor is at least 20 times greater than the binding affinity of said agonist for the A1 adenosine receptor.

In a preferred embodiment, an A3RAg has a binding affinity (KO for the human A3 adenosine receptor in the range of less than 200 nM, typically less than 100 nM, preferably less than 50 nM, more preferably less than 20 nM and even more preferably less than 10 nM. The lower the Ki, the lower the dose of the A3RAg that may be used that will be effective in activating the A3R and thus achieving the desired effect. Thus in certain embodiments, an A3RAg that has a $K_i$ for the human A3R of less than 5 nM and even less than 1 nM may be preferred.

In preferred embodiments, the A3RAg specifically activates the A3R at the administered levels, and is substantially devoid of activity in activating any of the other adenosine receptors i.e. the A1, A2a and A2b adenosine receptors. In particular, if the administered level of an A3RAg is such that its blood level reaches a level approaching that of the $K_i$ of the A1, A2a or A2b adenosine receptors, activation of these receptors may occur following such administration, in addition to activation of the A3R An A3RAg is thus preferably administered at a dose such that the blood level that will be attained will give rise to essentially only A3R activation.

A3 adenosine receptor agonists which are useful in the present invention include a variety of nucleoside derivatives which are known to act as A3 adenosine receptor agonists. As used herein, the term "nucleoside" refers to a compound comprising a sugar backbone, preferably ribose or deoxyribose, linked to a purine or pyrimidine base by way of N-glycosyl link. The term "nucleoside-derivative" denotes herein a synthetic nucleoside or a nucleoside which underwent chemical modifications by way of insertion/s, deletion/s or exocyclic and endocyclic substitution/s of group/s therein or conformational modifications which provide a derivative with the desired biological effect, such as enhancing melanin production and/or secretion, thereby increasing pigmentation in skin.

In accordance with particular embodiments of the present invention, the desired biological effect caused by an A3 adenosine receptor agonist is enhancement of melanin synthesis and/or secretion and/or accumulation in a skin cell. A3 adenosine receptor agonists useful for the invention include $N^6$-benzyladenosine-5'-uronamide derivatives, especially those containing a methyl- or ethyl-substituted uronamide moiety, which have been shown to possess significant A3 adenosine receptor affinity and selectivity. A well known A3 adenosine receptor agonist is $N^6$-(3-iodo-benzyl)-adenosine-5'-N-methyluronamide (IB-MECA) which is known to be 50-fold selective for the A3 adenosine receptor versus either the A1 or A2A receptors.

The A3 adenosine receptor agonist may in particular be an $N^6$-substituted-adenosine-5'-uronamide, such as an $N^6$-monosubstituted-adenosine-5'-uronamide or an $N^6$-disubstituted-adenosine-5'-uronamide.

In some embodiments, the A3 adenosine receptor agonist may be one categorized as an $N^6$-benzyladenosine-5'-uronamide; an $N^6$-4-substituted-sulfonamidophenylcarbamoyl-adenosine-5'-uronamide; a 2-chloro-$N^6$-substituted-4'-thio-adenosine-5'-uronamide; or an (N)-methanocarba adenosine-5'-uronamide. Derivatives and analogs of compounds in these various classes may also be used.

According to other particular embodiments, the A3 adenosine receptor agonist is selected from the group consisting of $N^6$-(3-iodobenzyl) adenosine-5'-(N-methyluronamide) (IB-MECA); 2-chloro-$N^6$-(3-iodobenzyl)-adenosine-5'-(N-methyluronamide) (C1-IB-MECA); $N^6$-(4-amino-3-iodobenzyl)-adenosine-5'-(N-methyluronamide) (AB-MECA); $N^6$-2-(4-aminophenyl)ethyladenosine (APNEA); 2-(1-hexynylhexynyl)-N-methyladenosine; 2-chloro-$N^6$-(3-iodobenzyl)-9-[5-(methylcarbamoyl)-D-ribofuranosyl]adenine (CF-102).

Some other agonistic compounds include (2S,3S,4R,5R)-3-amino-5-[6-(2,5-dichlorobenzylamino)purin-9-yl]-4-hydroxytetrahydrofuran-2-carboxylic acid methyl amide (CP-532,903); and ring-constrained (N)-methanocarba-5'-uronamide 2,$N^6$-disubstituted adenine nucleosides such as (1'R,2'R,3'S,4'R,5'S)-4-{2-chloro-6-[(3-chlorophenylmethyl)amino]purin-9-yl}-1-(methylaminocarbonyl)bicyclo [3.1.0]hexane-2,3-diol (MRS-3558; Tchilibon et al., 2005, J. Med. Chem., 48:1745-58; Melman et al Bioorg Med Chem Lett 2008 May 1; 18(9):2813-2819; Tosh et al., Bioorg Med Chem 2010 Jan. 15; 18(2):508-17).

In a particular embodiment, the A3 adenosine receptor agonist is selected from the group consisting of $N^6$-(3-iodobenzyl) adenosine-5'-(N-methyluronamide) (IB-MECA); 2-chloro-$N^6$-(3-iodobenzyl)-adenosine-5'-(N-methyluronamide) (C1-IB-MECA); 2-(1-hexynylhexynyl)-N-methyladenosine; 2-chloro-$N^6$-(3-iodobenzyl)-9-[5-(methylcarbamoyl)-D-ribofuranosyl]adenine (CF-102); and (2S,3S,4R,5R)-3-amino-5-[6-(2,5-dichlorobenzylamino)purin-9-yl]-4-hydroxytetrahydrofuran-2-carboxylic acid methyl amide (CP-532,903).

Selective A3 adenosine receptor agonists include thionucleoside analogs of IB-MECA, such as those described in WO 2004/038006 and U.S. Pat. No. 7,199,127, including for example (2R,3S,4R)-2-[2-chloro-6-(3-iodobenzylamino)purin-9-yl]-3,4-dihydroxytetrahydrothiophene-2-carboxylic acid methyl amide; (2S,3S,4R,5R)-5-(2-chloro-6-methylaminopurin-9-yl)-3,4-dihydroxytetrahydrothiophene-2-carboxylic acid methyl amide; and (2S,3S,4R,5R)[5-(2-chloro-6-(3-iodobenzyl amino)purin-9-yl)-3,4-dihydroxytetrahydrothiophene-2-carboxylic acid methyl amide.

Selective A3 adenosine receptor agonists further include thioadenosine analogs of C1-IB-MECA, as disclosed for example in Jeong et al., J Med Chem 2003:46:3775-3777; Jeong et al., J Med Chem 2006: 49:273-281; and Choi et al., Bioorg Med Chem 2009 Dec. 1; 17(23):8003-11.

A3 adenosine receptor agonists comprising a bicyclic ring substituent are described in U.S. Pat. No. 7,414,036, and include for example, $N^6$-(4-iodo-2-picolyl)-adenosine-5'-N-methyluronamide; $N^6$-(4-methyl-2-picolyl)-adenosine-5'-N-methyluronamide; $N^6$-(2-picolyl)-adenosine-5'-N-methyluronamide; $N^6$-(6-acetyl-2-picolyl)-adenosine-5'-N-methyluronamide; $N^6$-(4-iodo-2-picolyl)-2-(2-phenyl-1-ethynyl)-adenosine-5'-N-methyluronamide; and $N^6$-[(2-dimethylamino-7-iodo-1,3-benzoxazol-5-yl)-methyl]-adenosine-5'-N-methyluronamide.

$N^6$-4-sulfonamido-adenosine-5'-uronamide derivatives which are selective A3 adenosine receptor agonists are disclosed in U.S. Pat. No. 7,511,133 and in Baraldi et al., J. Med. Chem. 2004 Oct. 21; 47(22):5535-40, and include for example, 1-deoxy-1-[6-[[[[4-[N-(allyl)-N(methyl)aminosulfonyl]phenyl]amino]carbonyl]amino]-9H-purin-9-yl]-N-ethyl-β-D-ribofuranuronamide; 1-deoxy-1-[6-[[[(4-(N-methyl-N-isopropyl-amino-sulfonyl)-phenyl)-amino] carbonyl]amino]-9H-purin-9-yl]-N-ethyl-β-D-ribofuranuronamide; 1-deoxy-1-[6-[[[[4-[N,N-(dimethyl) amino-sulfonyl]phenyl]-amino]carbonyl]amino]-9H-purin-9-yl]-N-ethyl-β-D-ribofuranuronamide; and 1-deoxy-1-[6-[[[[4-[N,N-bis(allyl)amino-sulfonyl]phenyl]amino]carbonyl]amino]-9H-purin-9-yl]-N-ethyl-β-D-ribofuranuronamide; 1-deoxy-1-[6-[[[[4-[N,N-bis(ethyl)amino-sulfonyl] phenyl]amino]carbonyl]amino]-9H-purin-9-yl]-N-ethyl-β-D-ribofuranuronamide.

Various other A3 adenosine receptor agonists may be used in the invention, such as those disclosed for example in U.S. Pat. Nos. 5,688,774; 5,773,423; 5,573,772; 5,443,836; 6,048,865; 6,177,444; 6,194,449; 6,323,214; 7,199,127; 7,414,036; 7,465,715; 7,511,133; U.S. Patent Application No. 2005/0250729; WO 95/02604; WO 99/20284; WO 99/06053; WO 97/27173; WO 01/23399; WO 02/055085; WO 02/070532; and WO 2004/038006.

A3 Adenosine Receptor Antagonists

As used herein, an A3 adenosine receptor antagonist is any compound capable of specifically binding to the A3 adenosine receptor (A3R), and capable of fully or partially inhibiting i.e. inactivating said receptor. The A3 adenosine receptor antagonist is thus a compound that exerts its prime effect though the binding and inactivation of the A3R. Binding and functional assays that may be used for the characterization of such antagonists are essentially those that are used for the characterization of A3 adenosine receptor agonists, as described herein.

In particular embodiments, the A3 adenosine receptor antagonist has a binding affinity (Ki) for the A3 adenosine receptor that is less than about 200 nM, preferably less than about 100 nM, more preferably less than about 50 nM, even more preferably less than 10 nM. In other embodiments, the binding affinity of the A3 adenosine receptor antagonist for the adenosine A3 receptor is at least 20 times greater than the binding affinity of said antagonist for the A1 adenosine receptor.

A3 adenosine receptor antagonists which are useful in the present invention include a variety of known A3 adenosine receptor antagonists selected from but not limited to compounds variously classified as xanthines and derivatives thereof (as disclosed for example in Priego et al., J Med Chem. 2002 Aug. 1; 45(16):3337-44; and Muller et al., J Med Chem. 2002 Aug. 1; 45(16):3440-50; dihydropyridines and derivatives thereof (as disclosed for example in Jiang et al., 1997, J. Med. Chem. 40:2596-608 and U.S. Pat. No. 6,376,521); pyridines and derivatives thereof (as disclosed for example in Li et al., 1999, J. Med. Chem. 42:706-21); flavonoids and derivatives thereof (as disclosed for example in Ji et al., 1996, J. Med. Chem., 39:781-8); isoquinolines and derivatives thereof (as disclosed for example in van Muijlwijk-Koezen et al., J Med Chem. 2000 Jun. 1; 43(11): 2227-38; and Gao et al., Mol Pharmacol. 2001 November; 60(5):1057-63); triazoloquinazolines and derivatives thereof (as disclosed for example in Kim et al., J. Med Chem. 1996 Oct. 11; 39(21):4142-8); triazolonaphthiridines and derivatives thereof, thiazolopyrimidines and derivatives thereof, 2-arylpyrazolo[3,4-c]quinoline derivatives, 5-N-(phenylcarbamoyl)amino-8-2-(2-furyl)pyrazolo[4,3-e]-1,2,4-triazolo [1,5-c]pyrimidine derivatives (as disclosed for example in Baraldi and Borea, 2000, TiPS, 21:456-9); imidazoquinolines and derivatives thereof (as disclosed for example in U.S. Patent Application No. 2008/0255110); triazolopurines and derivatives thereof (as disclosed for example in U.S. Pat. No. 6,288,070); deazapurine derivatives (as disclosed for example in U.S. Pat. No. 7,504,407); and pyrazolo-triazolo-pyrimidine, triazolo-triazolo-pyrimidines and imidazolo-triazolo-pyrimidines and derivatives thereof (as disclosed for example in U.S. Pat. Nos. 7,470,698 and 6,448,253).

Particular examples of A3 adenosine receptor antagonists include 3-propyl-6-ethyl-5[(ethylthio)carbonyl]-2-phenyl- 4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl]ester (MRS-1334); 3-ethyl-5-benzyl-2-methyl-4-phenylethynyl-6-phenyl-1,4-(±)-dihydropyridine-3,5 dicarboxylate (MRS-1191); 3-ethyl 5-benzyl-2-methyl-6-phenyl-4-styryl-1,4-(±)-dihydropyridine-3,5-dicarboxylate (MRS-1097); 5-n-butyl-8-(4-trifluoromethylphenyl)-3H-[1,2,4]triazolo-[5,1-i]purine (OT-7999); (2R,3R,4S,5S)-2-[N$^6$-3-iodobenzyl)adenos-9'-yl]-7-aza-1-oxa-6-oxospiro[4,4]-nonan-4,5-diol (MRS-1292); N-(2-methoxyphenyl)-N'-[2-(3-pyridinyl)-4-quinazolinyl]-urea (VUF-5574); (8R)-8-ethyl-1,4,7,8-tetrahydro-4-5H-imidazo[2,1-i]purin-5-one (PSB-11); 2-phenoxy-6-(cyclohexylamino)purine (MRS-3777); 5N-(4-methoxyphenylcarbamoyl)amino-8-propyl-2-(2-furyl) pyrazolo[4,3-e]-1,2,4-triazolo[1,5-c]pyrimidine (MRE3008F20) and derivatives and analogs thereof.

In a particular embodiment, the A3 adenosine receptor antagonist is selected from the group consisting of 3-propyl-6-ethyl-5[(ethylthio)carbonyl]-2-phenyl-4-propyl-3-pyridine carboxylate (MRS-1523); 1,4-dihydro-2-methyl-6-phenyl-4-(phenylethynyl)-3,5-pyridinedicarboxylic acid 3-ethyl-5-[(3-nitrophenyl)methyl]ester (MRS-1334); and 3-ethyl-5-benzyl-2-methyl-4-phenylethynyl-6-phenyl-1,4-(±)-dihydropyridine-3,5 dicarboxylate (MRS-1191).

Suitable antagonists further include those disclosed in Jacobson et al., 1997, Neuropharmacology, 36:1157-65; Yao et al., 1997, Biochem. Biophys. Res. Commun, 232:317-22; Kim et al., 1996, J. Med. Chem., 39:4142-48; van Rhee et al., 1996, Drug Devel. Res., 37:131; van Rhee et al., 1996, J. Med. Chem., 39:2980-9; Siquidi et al., 1996, Nucleosides, Nucleotides 15:693-718; van Rhee et al., 1996, J. Med. Chem., 39:398-406; Jacobson et al., 1995, Drugs of the Future, 20:689-699; Jacobson et al., 1995, J. Med. Chem., 38:1720-35; Karton et al., 1996, J. Med. Chem., 39:2293-2301; Kohno et al., 1996, Blood, 88:3569-74; Jiang et al., 1996, J. Med. Chem., 39:4667-75; Yao et al., 1997, Biochem. Biophys. Res. Commun 232:317-22; and Jiang et al., 1996, J. Med. Chem. 40:2596-2608; Jeong L. S., 2008, Nucleic Acids Sympo. Series., 52: 79-80, Choi et al., Nucleic Acids Synp Ser (Oxf). 2008; (52):645-646; U.S. Pat. No. 7,435,740 and U.S. Patent Applications Nos. 2004/0067932 and 2006/0178385.

Allosteric Enhancers

The compositions and methods of the invention for increasing melanin production may further comprise the use of an allosteric enhancer of the A3 adenosine receptor. Such allosteric enhancers are disclosed for example in Gao et al., Mol Pharmacol. 2002 July; 62(1):81-9; Gao et al., Mol Pharmacol. 2001 November; 60(5):1057-63; and Goblyos et al., J Med Chem. 2006 Jun. 1; 49(11):3354-61.

Specific examples of allosteric enhancers of the A3 adenosine receptor include, but are not limited to, 1H-imidazo[4,5-c]quinolin-4-amines, 3-(2-pyridinyl)isoquinolines and 2,4-disubstituted quinolones. For example 1H-imidazo[4,5-c]quinolin-4-amine include N-(3,4-dichloro-phenyl)-2-cyclohexyl-1H-imidazo[4,5-c]quinolin-4-amine (LUF-6000); N-phenyl-2-cyclopentyl-1H-imidazo[4,5-c]quinolin-4-amine (DU124183). The 3-(2-pyridinyl)isoquinoline may be selected from 4-methoxy-N-[7-methyl-3-(2-pyridinyl)-1-isoquinolinyl]benzamide (VUF5455); 4-methyl-N-[3-(2-pyridinyl)-1-isoquinolinyl]benzamide (VUF8502); 4-methoxy-N-[3-(2-pyridinyl)-1-isoquinolinyl]benzamide (VUF8504); and N-[3-(2-pyridinyl)-1-isoquinolinyl]benzamide (VUF8507). The 2,4-disubstituted quinoline may be selected from N-(2-anilinoquinolin-4-yl)cyclopentanecarboxamide; N-{2-[(3,4-dichlorophenyl)amino]quinolin-4-yl}cyclopentanecarboxamide; N-[2-(benzylamino)quinolin-4-yl]cyclopentanecarboxamide; N-{2-[(4-methylphenyl)amino]quinolin-4-yl}cyclopentanecarboxamide; N-[2-(2,3-dihydro-1H-inden-5-ylamino)quinolin-4-yl]cyclopentanecarboxamide; N-{2-[(4-methoxyphenyl)amino]quinolin-4-yl}cyclopentanecarboxamide; N-{2-[(4-chlorophenyl)amino]quinolin-4-yl}cyclopentanecarboxamide; N-[2-(cyclopentylamino)quinolin-4-yl]cyclopentanecarboxamide; N-[2-(1H-indazol-6-ylamino)quinolin-4-yl]cyclopentanecarboxamide; N-(2-anilinoquinolin-4-yl)cyclohexanecarboxamide; N-{2-[(3,4-dichlorophenyl)amino]quinolin-4-yl}cyclohexanecarboxamide; N-{2-[(4-methylphenyl)amino]quinolin-4-yl}cyclohexanecarboxamide N-[2-(2,3-dihydro-1H-inden-5-ylamino)quinolin-4-yl]cyclohexanecarboxamide; N-(2-anilinoquinolin-4-yl)benzamide; N-{2-[(3,4-dichloro-phenyl)amino]quinolin-4-yl}benzamide; N-(2-anilinoquinolin-4-yl)-2-furamide; N-{2-[(3,4-dichlorophenyl)amino]quinolin-4-yl}-2-furamide; N-(2-anilinoquinolin-4-yl)cyclobutanecarboxamide; and N-{2-[(3,4-dichlorophenyl)amino]quinolin-4-yl}cyclobutanecarboxamide.

Adjunct Ingredients

The skin lightening compositions of the invention may further contain at least one other adjunct ingredient in addition to the specific A3 adenosine receptor antagonist. Adjunct ingredients include, but are not limited to, hydroxytetronic acid and/or hydroxytetronic acid derivatives, tetronic acid and/or tetronic acid derivatives, hydroquinone, α-hydroxy acids, and fatty acid esters of ascorbic acid. According to some embodiments some whitening compositions of the invention employ more than one adjunct ingredient.

Especially preferred whitening compositions of the invention that contain an adjunct ingredient employ either a hydroxytetronic acid and/or hydroxytetronic acid derivatives as those described in U.S. Pat. No. 7,019,029 or tetronic acid (2,4-furandione, formula $C_4H_6O_5$), or a tetronic acid derivative, or hydroquinone (sometimes also called p-dihydroxybenzene or 1,4 benzenediol), or both, in addition to the hydroxytetronic active ingredient in the formulation. Tetronic acid and its derivatives have been suggested to be useful in the suppression of melanin production by inhibiting tyrosinase and tyrosine phosphatases (Sodeoka, M., 2001, J. Med. Chem. 44:3216-22), which can augment the overall skin whitening observed when compositions of the invention are applied to skin, as does hydroquinone. Preferred tetronic acid adjunct ingredients are tetronic acid derivatives that inhibit tyrosinase or tyrosine phosphatase. These typically have an acyl or other hydrophobic group in the 3-position and a free tetronic acid moiety such as 5-(4-benzoylbenzoyl)oxymethyl-3-hexadecanoyltetronic acid reported by Sodeoka, et al., cited above. Other non-limiting examples include 3-hexadecanoyl-5-methanesulfonyloxymethyltetronic acid, 3-hexadecanoyl-5-methyltetronic acid, and 3-hexadecanoyltetronic acid. Typical tetronic acid or tetronic acid derivative and/or hydroquinone concentrations range from about 0.25% to about 25% by weight, more narrowly from about 1% to about 5%, and even more narrowly from about 2% to about 4% by weight.

As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are those which are less bulky structurally, typically having a one- to three-carbon backbone, so that they penetrate the skin well such as those disclosed in U.S. Pat. No. 5,965,618. Where employed, glycolic and/or lactic acid or their derivatives are preferred. Lactic acid was suggested as a skin-whitening agent in U.S. Pat. No. 5,262,153. Typical hydroxy acid concentrations range from about 1% to about 25% by weight, more specifically from about 2% to about 15%, and even more specifically from about 3% to 10% by weight. Typical hydroxytetronic acid concentrations range from about 8% to 12% by weight; more specifically from about 3% to about 7% by weight.

Fat-soluble fatty acid esters of ascorbic acid (vitamin C) are employed as alternate or additional adjunct ingredients in other embodiments, alone or in combination with hydroquinone or α-hydroxy acids. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. The esters may be prepared using hydrogenated oils or fats, or fractions thereof. Ascorbyl stearate prepared using canola oil, for example, commonly contain about 4% ascorbyl palmitate. It is an advantage of the invention that where fatty acid esters of ascorbic acid are employed as an adjunct ingredient, they help provide emollient properties to the composition. Typical concentration ranges of ascorbyl palmitate vary from about 0.25% to about 10%, more narrowly from about 2% to about 8%, and even more narrowly from about 3% to about 5% by weight.

Therapeutic Uses, Administration and Formulations

The invention encompasses therapeutic uses of A3 adenosine receptor antagonists for treating and ameliorating skin hyper-pigmentation disorders and conditions, as well as therapeutic uses of A3 adenosine receptor agonists for treating and ameliorating skin hypo-pigmentation disorders and conditions. Hyper-pigmentation conditions which may be treated with the invention include for example, pigmented spots, lentigo senilis, freckles, café au lait spots, liver spots, ephelides, periorbital darkening, post-inflammatory hyper-pigmentation, pigmented keratosis, melasma and chloasma.

Hypo-pigmentation conditions which may be treated with the invention include for example, pigmented vitiligo, piebaldism, leukoderma due to cicatrisation, and nevus depigmentosis.

These and other abnormal or undesirable skin pigmentation conditions are well understood by those of skill in the art, and are described for example in: Rose, Pigmentary disorders. Med Clin North Am. 2009 November; 93(6): 1225-39; Tones et al., Melasma and other disorders of hyperpigmentation. In: Cutaneous Medicine and Surgery. Arndt K A, LeBoit P E, Robinson J K, and Wintroub B U, eds. W.B. Saunders Co: Philadelphia, 1996, pp. 1233-1241; Young et al., Melasma update. Actas Dermosifiliogr. 2009 December; 100 Suppl 2:110-3; Taylor et al., Postinflammatory hyperpigmentation. J Cutan Med Surg. 2009 July-August; 13(4):183-91; Hershkovitz et al., Monogenic pigmentary skin disorders: genetics and pathophysiology. Isr Med Assoc J. 2008 October; 10(10):713-7; Ramos-e-Silva et al., Hair, nail, and pigment changes in major systemic disease. Clin Dermatol. 2008 May-June; 26(3):296-305; Yu et al., Diagnosis and treatment of pigmentary disorders in Asian skin Facial Plast Surg Clin North Am. 2007 August; 15(3):367-80, vii; Dessinioti et al., A review of genetic disorders of hypopigmentation: lessons learned from the biology of melanocytes. Exp Dermatol. 2009 September; 18(9):741-9.

A preferred subject to be treated is a human.

Further encompassed within the invention are cosmetic uses of A3 adenosine receptor antagonists for lightening dark skin, for example in individuals of population groups having genetically dark skin. Further encompassed within the invention are cosmetic uses of A3 adenosine receptor agonists for producing a tanned skin effect in individuals having fair skin.

Further encompassed within the invention is the use of A3 adenosine receptor agonists for treating depigmentation of a skin site which occurs secondary to surgical skin graft procedures, and the use of A3 adenosine receptor antagonists for treating hyperpigmentation of a skin site which occurs secondary to surgical skin graft procedures. It is well known in the art that skin graft procedures may result in depigmentation or hyper-pigmentation at the graft site. Such an undesirable outcome may occur following cosmetic surgery, burn treatment, in particular split-thickness grafts or any other medical intervention requiring a skin graft procedure.

The cosmetic and pharmaceutical compositions comprising as and active ingredient an A3 adenosine receptor agonist or an A3 adenosine receptor antagonist may be administered to a subject by any route, including but are not limited to, direct administration into, onto or in the vicinity of hyper-pigmented or hypo-pigmented tissue, topical, intradermal, transdermal, subcutaneous, parenteral (including intravenous, intraarterial, intramuscular, intraperitoneal administration), as well as intranasal and oral administration. The compounds can be administered by any convenient route and can be administered together with other therapeutically active agents, such as an allosteric enhancer of the A3 adenosine receptor or an adjunct skin lightening or whitening agent as described herein. According to some embodiments, the route of administration is a route which enables the active ingredient i.e. A3 adenosine receptor agonist or A3 adenosine receptor antagonist to reach the blood stream, suitably intramuscular, intraperitoneal, intravenous, subcutaneous, intranasal or oral administration.

It may be desirable to administer the cosmetic or pharmaceutical composition of the invention locally to the hyper-pigmented or hypo-pigmented tissue in need of treatment; this can be achieved by, for example, and not by way of limitation, local injection or topical application, e.g., in conjunction with a wound dressing.

The terms "effective amount" and "amount effective" are used interchangeably herein to refer to the amount and/or dose of an A3 adenosine receptor ligand which achieves its intended purpose. In the case where increasing any of melanin production, secretion or accumulation is desired, for example for treating a hypo-pigmentation condition, an effective amount of an A3 adenosine receptor agonist is that which results in a measurable or detectable increase in melanin level or skin pigmentation or relevant change in melanin location within or among cells. Similarly, in the case where decreasing any of melanin production, secretion or accumulation is desired, for example for treating a hyper-pigmentation condition, an effective amount of an A3 adenosine receptor antagonist is that which results in a measurable or detectable decrease in melanin level or skin pigmentation or relevant change in melanin location within or among cells.

An example of an effective amount is a daily administration of an A3 adenosine receptor agonist within the range of between about 1 μg/kg body weight and about 10 mg/kg body weight. Such an amount of an A3 adenosine receptor agonist is typically administered in a single daily dose although at times a daily dose may be divided into several doses administered throughout the day or at times several daily doses may be combined into a single dose to be given to the patient once every several days, particularly if administered in a sustained or controlled release formulation.

Administration of the A3 adenosine receptor agonist or the A3 adenosine receptor may be carried out over a period of at least two weeks, or at least one month, or at least two months, or longer, in order to achieve the desired outcome.

The pharmaceutical compositions of the present invention may contain, for example, 0.1 to 99.5% (more preferably, 0.5 to 90%) of active ingredient in combination with a pharmaceutically acceptable carrier.

As used herein, the term "pharmaceutically acceptable carrier" means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. A carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

According to some embodiments, the compositions of the invention can be applied to the skin According to some other embodiments, the compositions of the invention can be applied to hair follicles. The compositions may be in the form of, for example, and not by way of limitation, an ointment, cream, gel, paste, foam, aerosol, pad or gelled stick.

A3 adenosine receptor agonists and antagonists according to the principles of the invention can be delivered in a controlled release system. In one embodiment, the A3 Adenosine receptor agonists and antagonists of the invention can be administered in combination with a biodegradable, biocompatible polymeric implant, which releases the A3 Adenosine receptor antagonist or agonist over a controlled period of time at the hyper-pigmented or hypo-pigmented tissue respectively. Examples of preferred polymeric materials include polyanhydrides, polyorthoesters, polyglycolic acid, polylactic acid, polyethylene vinyl acetate, copolymers and blends thereof (see Medical applications of controlled release, Langer and Wise (eds.), 1974, CRC Pres., Boca Raton, Fla.).

According to some preferred embodiments, the A3 adenosine receptor agonist or antagonist is administered as part of a topical formulation. The compositions of the present invention formulated for topical administration comprise the melanin modulating agent in an effective dose together with one or more pharmaceutically or therapeutically acceptable carriers and optionally other ingredients. Various considerations are described, e.g., in Gilman et al. (eds) (1990) The Pharmacological Bases Of Therapeutics, 8th Ed., Pergamon Press; Novel Drug Delivery Systems, 2nd Ed., Norris (ed.) Marcel Dekker Inc. (1989), and Remington's Pharmaceutical Sciences.

Typically, the formulations will comprise a preparation for delivering a melanin modulating agent directly to the skin or hair comprising the modulating agent, typically in concentrations in the range from about 0.001% to 20%; preferably, from about 0.01 to about 10%; more preferably, from about 0.1 to about 5%; together with a non-toxic, pharmaceutically acceptable topical carrier. Topical preparations can be prepared by combining the melanin modulating agent with conventional pharmaceutical diluents and carriers commonly used in topical dry, liquid, cream and aerosol formulations. Typically, the preparation of suitable dosage forms (e.g., sprays, ointments, pastes, creams, lotions, gels, and solutions) will comprise mixing the active compound under sterile conditions with diluents and carriers along with any preservatives, buffers, or propellants which may be required.

Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like.

Drops may be formulated with an aqueous base or non-aqueous base also comprising one or more dispersing agents, suspending agents, solubilizing agents, and the like.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

In some embodiments, active and/or adjunct ingredients are added to a sunscreen or sunblock formulations so that topical application has the further advantage of preventing repigmentation during and/or after treatment. Preferred formulae of this type are SPF 15 or higher. Many of these preferred embodiments contain titanium dioxide or zinc oxide which additionally smooth and lubricate the skin and help minimize side effects in sensitive skin.

Parenterally administered formulations are generally prepared in a unit dosage injectable form (solution, suspension, emulsion). A pharmaceutical formulation suitable for injection includes sterile aqueous solutions or dispersions and sterile powders for reconstitution into sterile injectable solutions or dispersions. The carrier employed can be a solvent or dispersing medium containing, for example, water, ethanol, polyol (for example, glycerol, propylene glycol, lipid polyethylene glycol and the like), suitable mixtures thereof and vegetable oils. Non-aqueous vehicles such as cottonseed oil, sesame oil, olive oil, soybean oil, corn oil, sunflower oil, or peanut oil and ester, such as isopropyl myristate, may also at times be used as solvent systems for the active ingredient.

Additionally, various additives which enhance the stability, sterility and isotonicity of the compositions, including antimicrobial preservatives, antioxidants, chelating agents and buffers can be added. Prevention of microbial growth can be ensured by inclusion of various preservatives, for example, parabens, chlorobutanol, phenol, sorbic acid and the like.

For the purpose of oral administration, the active ingredient may be formulated in the form of tablets, suspensions, solutions, emulsions, capsules, powders, syrups and the like.

In solid dosage forms for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The term "ameliorate" is used here in its broadest sense to refer to the reduction of the pigmentation in patients suffering from hyper-pigmentation. Alternatively, it refers to an increase in pigmentation in patient suffering from hypo-pigmentation. The term includes any of the arrest, prevention, decrease, and improvement in any of the symptoms of hyper-pigmentation and hypo-pigmentation, both temporary and long term. Amelioration of hyper-pigmentation or hypo-pigmentation is a further example of successful treatment or therapy.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods used for the Examples disclosed herein are as follows:

Reagents.

IB-MECA, MRS-1523 and IBMX were purchased from Sigma. For each reagent, a stock solution of 10 mM was prepared in dimethyl sulfoxide (DMSO), and further dilutions in DMEM medium (Dulbecco's modified Eagle's medium) were prepared. DMEM media, fetal calf serum, and antibiotics for cell cultures were obtained from Kibbutz Beit-Haemek, Israel. Kojic acid, synthetic melanin and anti-phospho-ERK antibody were purchased from Sigma. Anti-ERK-2 antibody and anti-phospho-ERK antibody were purchased from Santa Cruz Biotechnology. Anti-Akt-1 antibody and anti-phospho-Akt antibody were purchased from Cell Signaling, and anti-Mitf antibody was purchased from Abcam. BCA™ Protein Assay Kit and ECL Kit were purchased from Thermo Scientific.

Cell Cultures.

B16 F1 melanoma cells were grown adherently and maintained in DMEM (without phenol red), containing 10% fetal calf serum, 1% antibiotics (penicillin, streptomycin and nystatin, each at 100 U/ml), and 2 mM L-glutamine. Cells were cultured at 37° C. in 5% $CO_2$, and passaged two to three times weekly at a ratio of 1:10.

Melanin Assay.

Melanin content was determined as reported by Sato et al., (2008), *Biol. Pharm. Bull.*, 31(1):33-7, with modifications. Cells ($6.5 \times 10^4$) were seeded into 6 well plates with 5 ml of DMEM medium (described above) and incubated at 37° C. with 5% $CO_2$ for 3-4 hours to enable cell adherence. Cells were then exposed to test chemicals (IB-MECA, MRS-1523 or kojic acid) at the desired concentration and incubation periods. After the treatment, the supernatants were collected to determine the amount of melanin secreted to the medium. Cells were washed with PBS, detached by incubation with trypsin/EDTA and then DMEM with serum (0.75 ml) was added to each well. Cells were collected by centrifugation and lysed by exposure to 2N NaOH (1 ml) at 60° C. for 1 h and the melanin content was determined by measuring the absorption at 400 nm. The amount of protein in each lysate was determined using bovine serum albumin is used as the standard. The amount of melanin in each sample was calculated using synthetic melanin as standard. The results were expressed as the melanin content per mg protein (μg/mg protein). To compare among treatments, the results were expressed as percent relative to control.

Western Blot Analysis.

B16 melanocytes grown in 6-well plates were serum starved overnight and then incubated in the presence of IB-MECA or MRS-1523 (10 μM), for different time intervals at 37° C. Cells were then rinsed with ice cold PBS and lysed by addition of RIPA buffer containing: proteinase inhibitor (PIC, 1:50 v/v), 0.1 mM phenylmethylsulphonylfluoride (PMSF) and 1 mM sodium orthovandate. Cells debris was removed by centrifugation. The protein level in the supernatants was determined using BSA as standard. Equal amounts of the sample (20 μg) were separated by SDS-PAGE using 10% polyacrylamide gels. The resolved proteins were then electroblotted onto nitrocellulose membrane. Membranes were blocked with 1% bovine serum albumin and incubated with anti-ERK-2 antibody (1:1000) or anti-phospho-ERK antibody (1:10000) for 1 h at room temperature, or with anti-Akt-1 antibody (1:1000) or with anti-phospho-Akt antibody (1:000) at 4° C. for 24 h. Blots were then washed and incubated with horseradish peroxidase (conjugated secondary antibodies), for 1 hour at room temperature. The proteins were detected using ECL kit. For the detection of ERK phosphorylation after 72 hours of exposure to the ligands, non-starved cells were used (with 10% FCS).

Immunostaining and Confocal Microscopy.

B16 melanocytes were grown for 24 h on glass cover-slips coated with poly-L-lysine (500 ug/ml) in 6 wells plates in the presence of IB-MECA or MRS-1523 (10 μM), for 3 hr or 24 h at 37° C. Cells were fixed in 4% formaldehyde in phosphate buffered saline (PBS) for 1 h at room temperature. The fixed cells were rinsed three times for 1 min with PBS. To block non-specific interaction of the antibodies, cells were incubated with PBS (1% BSA, 0.1% Triton X-100). For staining with anti-phospho-Akt antibody, cells were incubated with the primary antibody at a dilution of 1:1000 for 24 h at 4° C. Cells were washed three times for 3 min with PBS and incubated with Cy3-conjugated donkey anti-rabbit antibody at a dilution of 1:250 in PBS for 2 h in the dark. Cells were washed three times with PBS and mounted with Fluoromount (Sigma). Cells were visualized by confocal microscopy (excitation 553 and emission at 568, Lieca).

For staining with anti-Mitf antibody, cells were treated as described above and incubated with primary anti-Mitf antibody at a dilution of 1:100 for 24 h at 4° C. and with the secondary antibody Alexa Fluor® 488-conjugated donkey anti-mouse antibody at a dilution of 1:250 for 2 h in the dark.

Skin Organ Culture.

Samples of human breast skin obtained during breast surgery were cut into pieces (0.5×0.5 cm) and cultured in DMEM medium (described above) in 6 well plates and incubated at 37° C. with 5% $CO_2$ for 12 days. Skin samples were topically treated with 10 or 50 μM of various A3 adenosine receptor ligands or 100 μM hydroquinone three times during the incubation period and the medium was exchanged every 3 days.

DOPA Staining.

Treated skin samples were washed with PBS and the epidermal sheets were separated from the dermis and incubated in 0.1% L-3,4-DOPA in PBS for 4 h at 37° C. The epidermis sheets were then fixed with 4% formaldehyde solution, dehydrated by graded alcohol, cleared in xylene, and mounted on glass slides.

Skin Melanin Evaluation.

DOPA positive melanocytes were visualized by light microscopy (×400 magnification). Light transmission capacity of the epidermis sheet was determined by taking 3 images of each sheet from different zones of the epidermis of each treatment (×50 magnification). Light transmission of each area in the epidermis sheet was calculated and expressed as a mean of density of three images.

Example 1

Figure 1B:
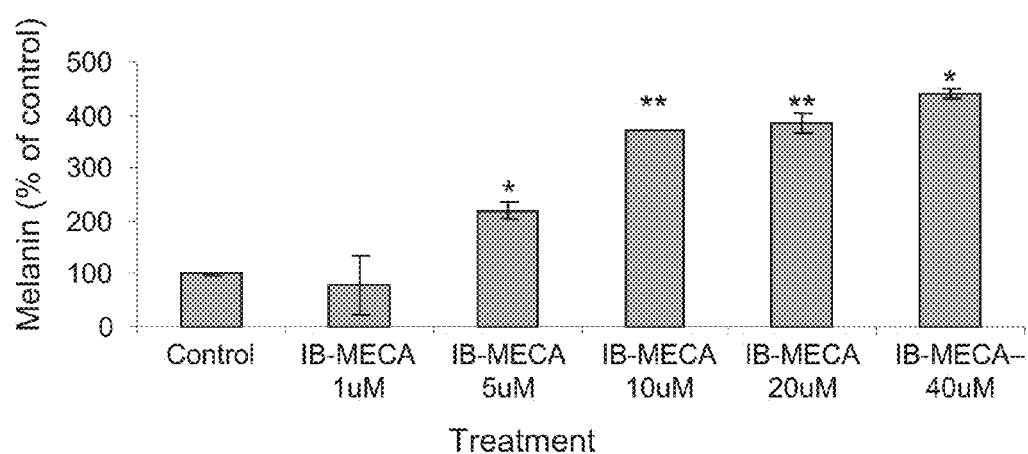
Figure 1C:
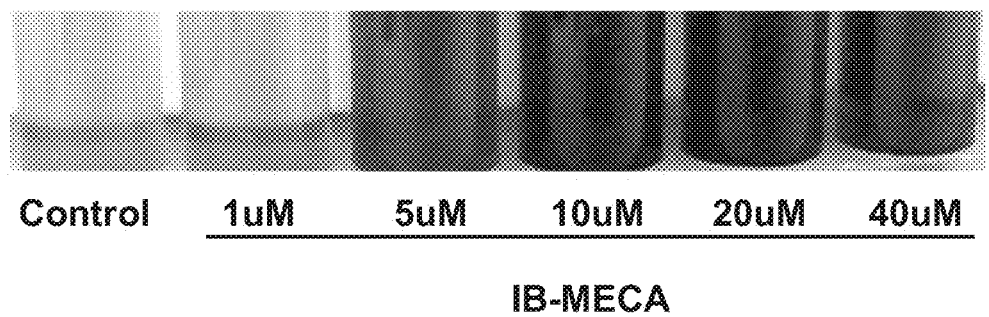

The A3 Adenosine Receptor Agonist IB-MECA Exerts a Stimulatory Effect on Melanin Synthesis and Secretion in B16 Melanocytes Treatment of B16 melanocytes with increasing doses of IB-MECA resulted in a dose dependent increase of the melanin level, as shown in FIG. 1. Specifically, as shown in FIG. 1A, at the highest IB-MECA concentration, the intracellular melanin level was increased by 143±4.1% while the secretion of melanin to the media was increased by 554±23.8% ($p<0.001$). As shown in FIG. 1B, exposure of the cells to 5 μM IB-MECA resulted in an increase of the total melanin level by 220±19.4% ($p<0.001$), while treatment with 10 μM of IB-MECA increased the total level by 369±1%, and treatment with 40 μM of IB-MECA increased the melanin level by 441±53.8%. Accordingly, the stimulatory effect of IB-MECA on the melanin level was attributable mainly to the increase in the secretion of melanin by B16 melanocytes (FIGS. 1A-1C).

Example 2

Figure 2A:
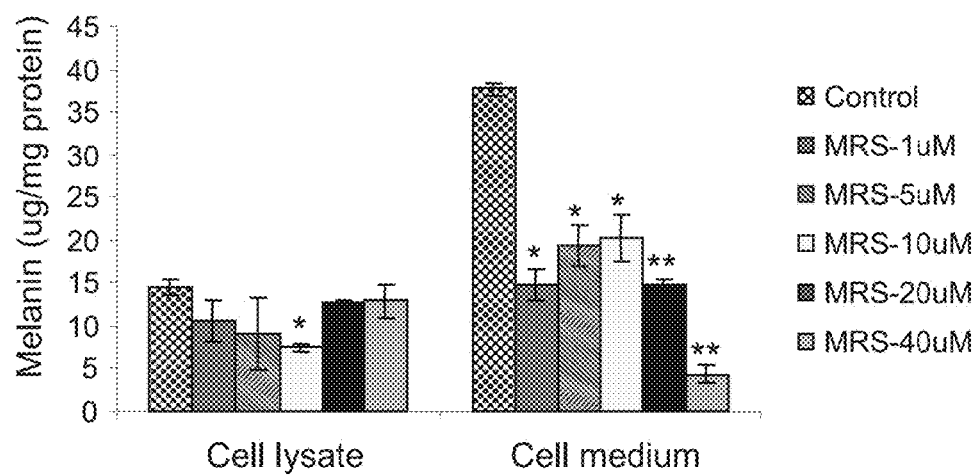
FIGS. 2A and 2B show the effect of the A3 adenosine receptor antagonist MRS-1523 (abbreviated as "MRS") on melanin synthesis and secretion in B16 melanocytes. Cells were cultured in 10% DMEM in the presence of various concentrations of MRS-1523 for 5 days. Levels of melanin in the media and in the cell lysates, and total protein content in the cell lysates were then determined as described in Materials and Methods. Melanin levels were measured and calculated separately for each sample.
Figure 2B:
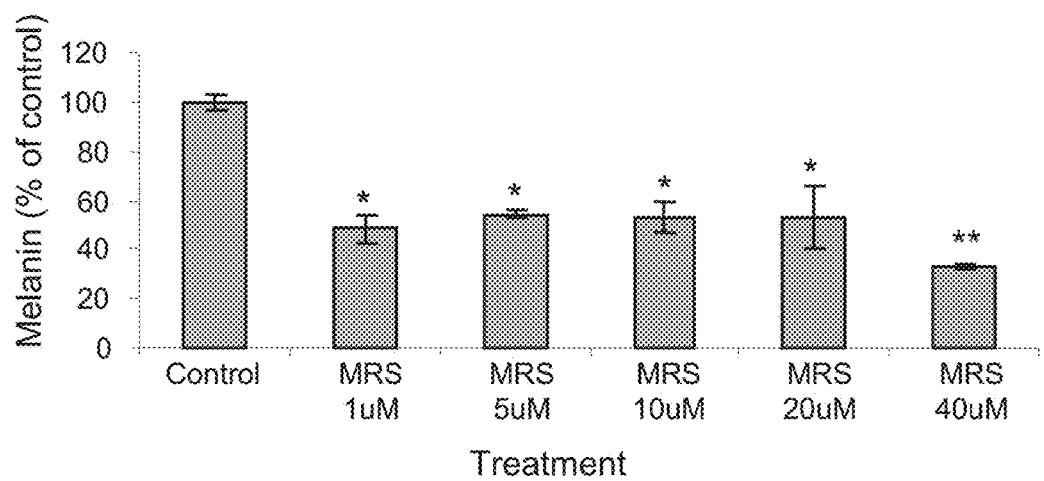

The A3 Adenosine Receptor Antagonist MRS-1523 Exerts an Inhibitory Effect on Melanin Synthesis in B16 Melanocytes MRS-1523 affected both the synthesis and the secretion of melanin by the cells as shown in FIG. 2. Exposure of melanocytes to 40 μM MRS-1523 caused a decrease in total melanin by 67±1.07% ($p<0.001$; FIG. 2B). This treatment effectively blocked melanin secretion by 88±1.7%, while the melanin level within the cells decreased only by 11±2.3% (FIG. 2A). Similarly, upon treatment of the cells with 1 μM and 5 μM MRS-1523, the melanin level in the cells decreased only by 27±5.7% and 24±1.7% respectively. However, this treatment was associated with a significant decrease of the intracellular melanin (48%±4.9, $p<0.05$). At all concentrations tested within the range of 1-40 μM MRS-1523, the secreted and the total melanin levels were lower than that of the control ($p<0.05$, FIGS. 2A and 2B).

At lower concentrations of MRS-1523 the modulating effect on melanin synthesis and secretion was less pronounced. Thus, the total melanin in melanocytes exposed to 1 μM and 5 μM MRS-1523 decreased by 37±5.7% and 24±1.9% respectively ($p<0.05$). At all MRS-1523 concentrations tested the secreted and the total melanin (melanin in cell and in media) were lower than that of the control ($p<0.05$, FIGS. 2A and 2B).

Example 3

Time-Dependent Melanin Synthesis and Secretion by B16 Melanocytes Treated with IB-MECA or MRS-1523

Figure 3A:
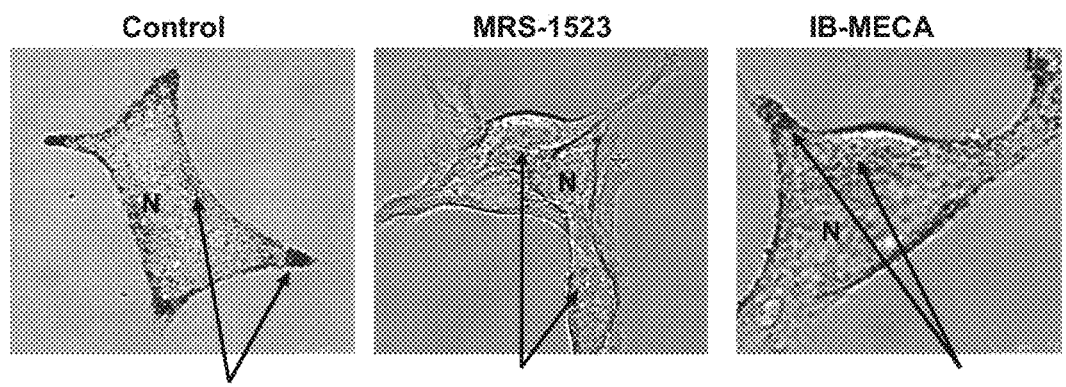
FIGS. 3A-3E show the time course of melanin synthesis and secretion by B16 melanocytes treated with IB-MECA or MRS-1523. Cells were exposed to 10 μM of IB-MECA or MRS-1523 and the melanin was monitored at different time intervals. Levels of melanin in the media and in the cell lysates, and total protein content in the cell lysates were determined as described in Materials and Methods. Melanin levels were measured and calculated separately for each sample.
Figure 3B:
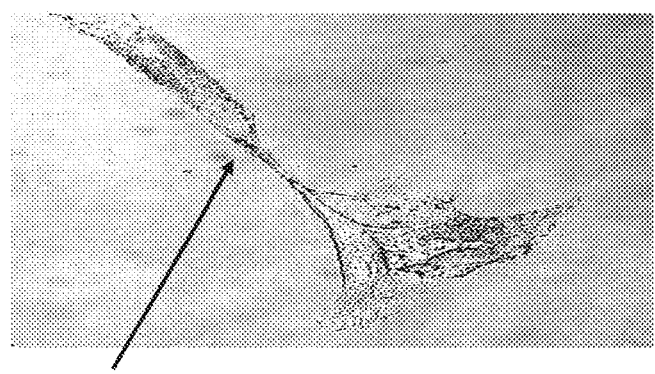
Figure 3C:
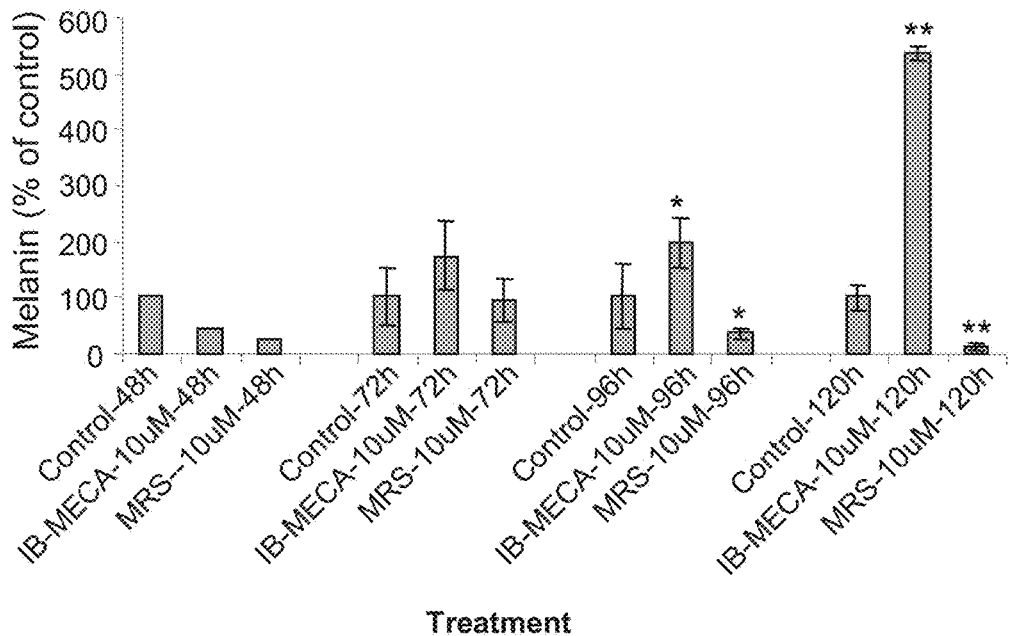
Figure 3D:
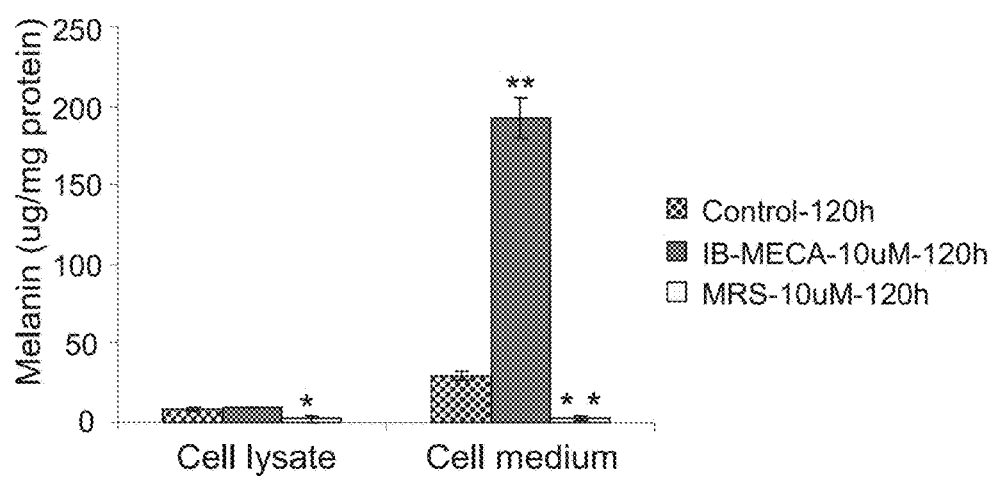

B16 melanocytes were exposed to 10 μM of IB-MECA or 10 μM MRS-1523 and the melanin levels in the cells and in the media were monitored at different time points following exposure to the ligands. The results indicated that detectable levels of melanin secreted to the medium (extracellular) were not observed after 24 hours of exposure to either IB-MECA or MRS-1523. However, as shown in FIG. 3A, confocal microscopy showed observable changes in melanin level and distribution in the cytosol of the treated cells. Specifically, more melansomes were observed in the cell periphery and in the dendritic sites of the control and IB-MECA treated melanocytes as compared to MRS-1523 treated cells (melansomes indicated by arrows). Moreover, in cells treated with IB-MECA, melanosomes were accumulated in the perinuclear areas (melansomes indicated by arrows). FIG. 3B depicts transfer of melanosomes from one melanocyte to the other by a dendrite-dendrite interaction. Moreover the melanosomes appear to be injected and moved along the edge of cells FIG. 3C shows total melanin levels after various intervals of exposure to IB-MECA or MRS-1523. After 72 hours of exposure to IB-MECA, the level of total melanin was non-significantly increased. However, after four days (96 h) of exposure to IB-MECA, the total melanin level (i.e. melanin in the cells and melanin secreted to the media) was significantly increased by $198\pm12.1\%$ ($p<0.05$). Similarly, after four days (96 h) of exposure to MRS-1523, the total melanin level was significantly decreased by $67\pm4.4\%$ ($p<0.05$). Exposure to IB-MECA for a period of 120 h resulted in an increase of $537\pm31.9\%$ in the total melanin level; this increase was attributed mainly to the enhanced secretion of melanin into the media (FIGS. 3C and 3D). A decrease of $88\pm1.3\%$ in the overall melanin level after 5 days of cells exposure to MRS-1523 was attributed to a similar decrease in melanin level in both the cells and the media ($p<0.001$).

Figure 3E:
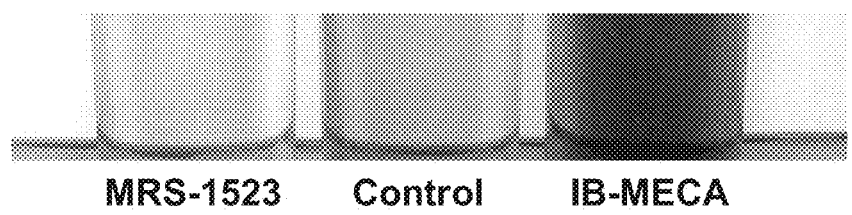

FIG. 3E is a photograph showing melanin secretion to the media in control cells and in cells exposed to IB-MECA or MRS-1523 for 5 days. Consistent with the results shown in FIGS. 3C and 3D, prolonged exposure of melanocytes to IB-MECA resulted in a visually observable increase in melanin, whereas prolonged exposure of cells to MRS-1523 resulted in a visually observable decrease in melanin.

Example 4

The Effect of Kojic Acid on Melanin Levels, Synthesis and Secretion in B16 Melanocytes Kojic acid is a well known melanization decreasing agent. The melanin synthesis in cells has been well studied; however, no information regarding the effect of kojic acid on melanin secretion, which constitutes a major contribution to skin melanization, was obtained. In order to evaluate the effect of kojic acid on the synthesis and secretion of melanin in cells, B16 melanocytes were cultured in 10% DMEM in the presence of different concentrations of kojic acid for 5 days. The melanin and protein content were measured as described in Materials and Methods.

Figure 4A:
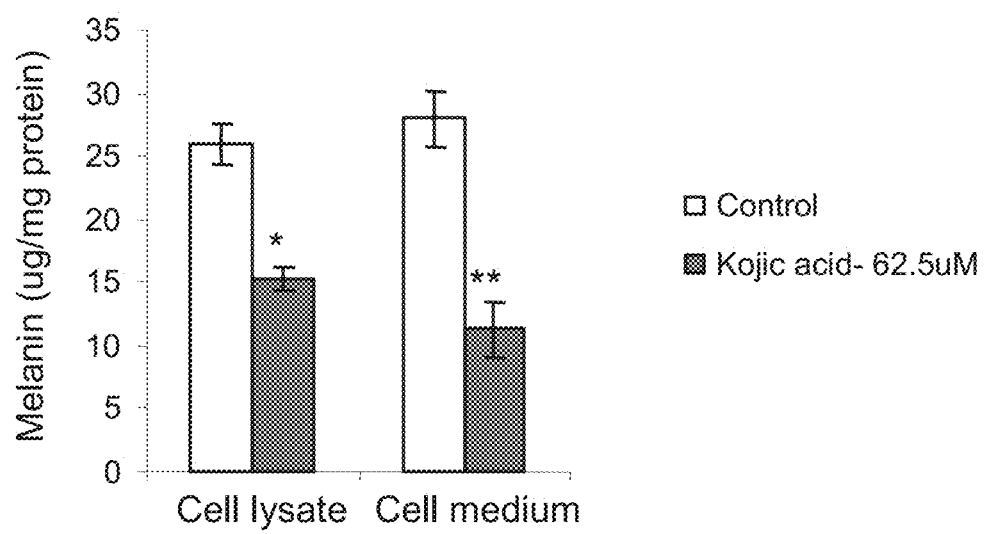
FIGS. 4A and 4B show the effect of kojic acid on melanin synthesis and secretion. B16 melanocytes were cultured in 10% DMEM in the presence of Kojic acid for 5 days. Levels of melanin in the media and in the cell lysates, and total protein content in the cell lysates were determined as described in Materials and Methods. Melanin levels were measured and calculated separately for each sample.
Figure 4B:
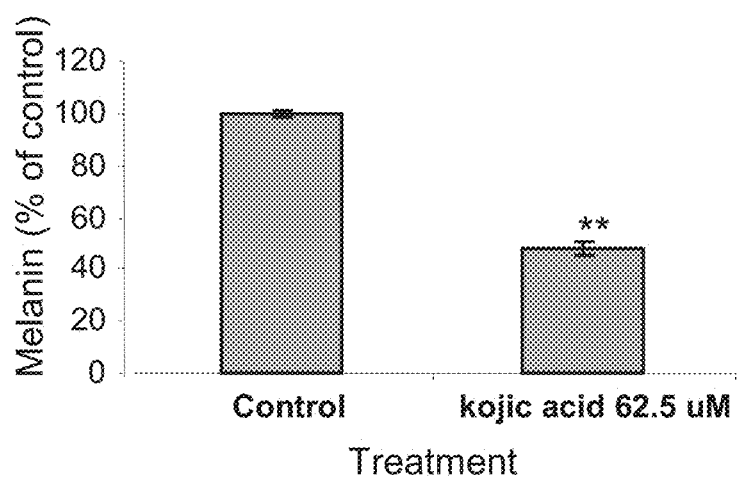

As shown in FIG. 4B, kojic acid exerted inhibition of $51\%\pm2.4$ in the total melanin level ($p<0.001$). FIG. 4A shows that both melanin synthesis (overall melanin levels) and secretion (melanin level in the medium) were affected.

Example 5

The Effect of A3 Adenosine Receptor Ligands on Akt Phosphorylation

Figure 5A:
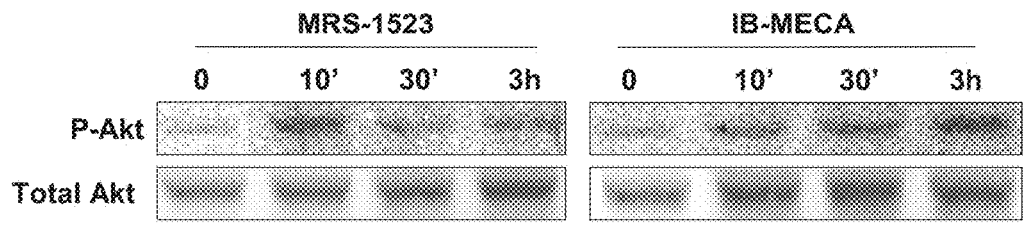
FIGS. 5A and 5B show the effect of A3 adenosine receptor ligands on Akt phosphorylation. Serum starved B16 melanocytes were exposed to 10 μM IB-MECA or MRS-1523 for 10 min, 30 min or 3 h.
Figure 5B:
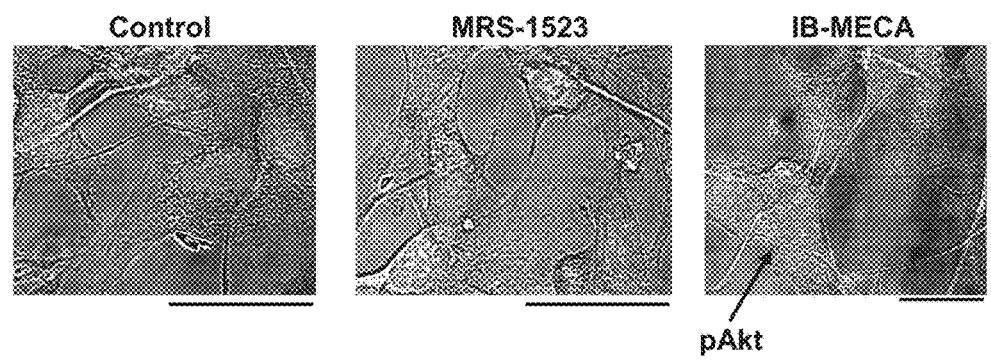

In order to explore the possible mechanisms involved in the modulation of melanin synthesis, exerted by IB-MECA in increasing melanin levels, and by MRS-1523 in decreasing melanin levels, the effects of short time exposure to both agents on Akt phosphorylation in B16 melanocytes were tested. Serum starved B16 melanocytes were exposed to 10 μM IB-MECA or MRS-1523 10-180 minutes, as indicated in FIGS. 5A and 5B. Cells were collected and protein was extracted and quantified as described in Materials and Methods. Proteins were analyzed for Akt phosphorylation and total Akt expression by western blot analysis (FIG. 5A). Cells treated for 3 h were analyzed by confocal microscopy (FIG. 5B).

The results shown in FIG. 5A indicate that both the A3 adenosine receptor agonist (IB-MECA) and the A3 adenosine receptor antagonist (MRS-1523) induced phosphorylation of Akt within 10 min. However, continued exposure to MRS-1523 (up to 3 h) led to downregulation of P-Akt (FIG. 5A left panel), while continued exposure to IB-MECA resulted in increased phosphorylation of Akt (FIG. 5A right panel).

The Akt family signal pathway has been shown to be upstream to the ERK signal pathway, and the increase in phosphorylated Akt is implicated in downregulation of phosphorylated ERK. Without wishing to be bound by any particular mechanism and theory, it is contemplated that increasing the level of phosphorylated ERK leads to downregulation of the transcription factor Mitf which regulates tyrosinase, a key enzyme in melanogenesis and cell differentiation.

Example 6

The Effect of A3 Adenosine Receptor Ligands on ERK Phosphorylation

Figure 6A:
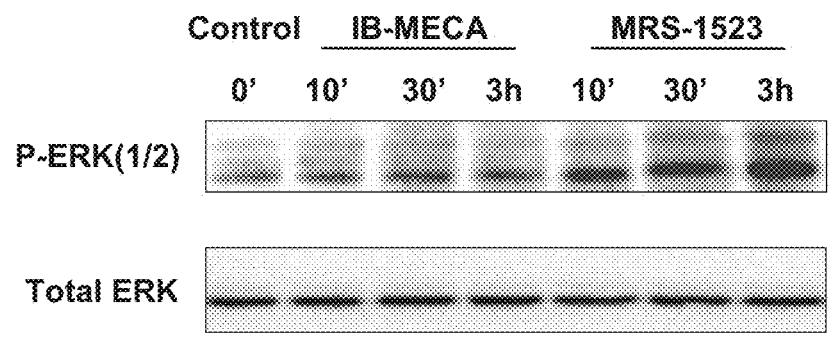
FIGS. 6A and 6B show the effect of A3 adenosine receptor ligands on ERK1/2 phosphorylation. Serum starved B16 melanocytes were exposed to 10 μM IB-MECA or MRS-1523 for various time periods, and protein extracts of the cells were analyzed by western blot analysis (20 μg protein/lane) for ERK phosphorylation and total ERK expression.

The ERK signaling pathway has been shown to be upstream to the transcription factor Mitf and downstream to the Akt signaling pathway. ERK phosphorylation analyses show that MRS-1523 induced phophorylation of ERK 1 within 30 minutes and phosphorylation of ERK 2 within 10 minutes (FIG. 6A). In contrast, IB-MECA (10 μM) did not increase the level of ERK phosphorylation (FIG. 6A).

Figure 6B:
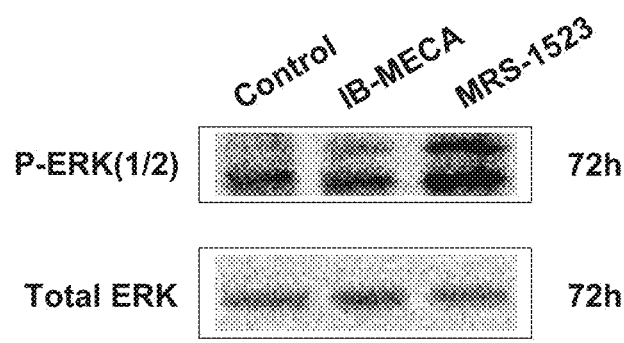

ERK phosphorylation in non-starved cultures (containing 10% FCS) after 72 hours of exposure to the ligands was examined. Exposure to MRS-1523, stimulated phosphorylation of both ERK1 and ERK 2, while exposure to IB-MECA did not appear to affect ERK phosphorylation. (FIG. 6B).

Example 7

Figure 7:
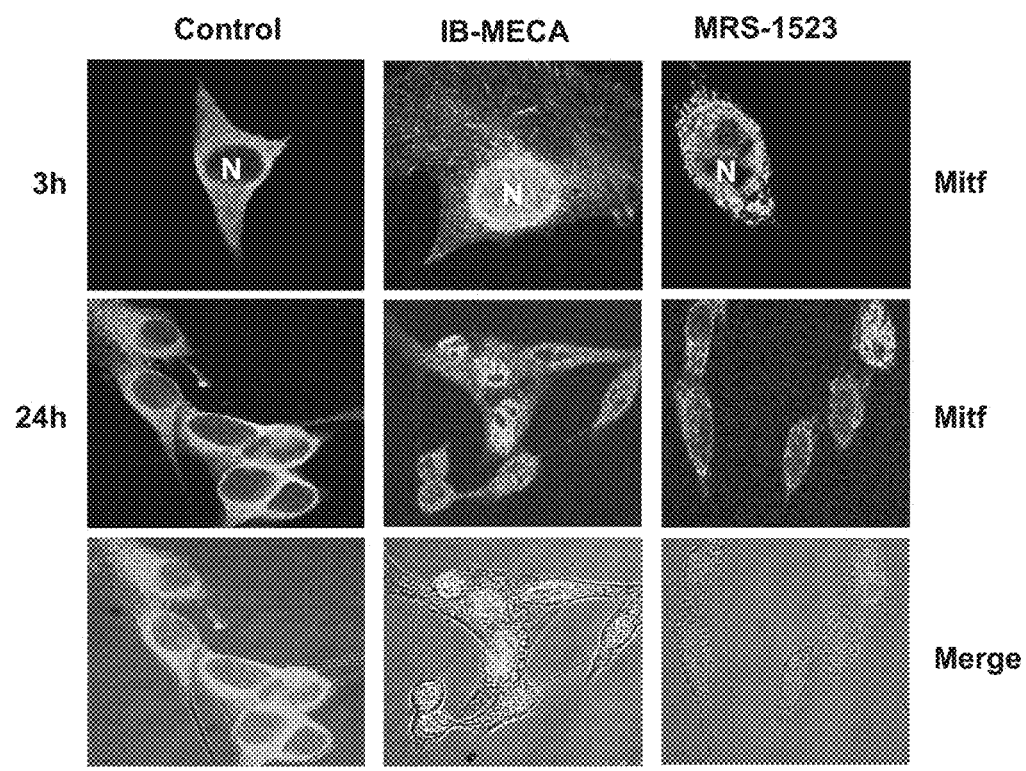
FIG. 7 shows Mitf expression and localization in B16 melanocytes treated with A3 adenosine receptor ligands for 3 h or 24 h, followed by immunostaining with anti-Mitf antibody and visualization by confocal microscopy. N, nucleus.

The Effect of A3 Adenosine Ligands on Mitf Expression and Localization in B16 Melanocytes Mitf is a transcription factor which regulates tyrosinase, a key enzyme in melanogenesis and cell differentiation and has been shown to be downstream to ERK. FIG. 7 shows that Mitf is highly expressed in the control and IB-MECA treated cells (FIG. 7, left and middle panels). Moreover, exposure of cells to the A3 adenosine receptor agonist IB-MECA induced translocation of Mitf protein to the nucleus within 3 h of exposure, while in control cells Mitf remained in the cytosol. After 24 h of exposure to A3 adenosine receptor agonist, the expression of Mitf in IB-MECA treated cells remained high, both in the cytoplasm and in the nucleus. In contrast, in the control cells Mitf expression was observed mainly in the cytosol. Furthermore, cells treated with the A3 adenosine receptor antagonist MRS-1523 exhibited very low Mitf expression both in the cytosol and in the nucleus (FIG. 7, right panels).

Without wishing to be bound by any particular mechanism or theory, the results disclosed herein support the conclusion that the effects of enhanced pigmentation exerted by IB-MECA and decreased pigmentation exerted by MRS-1523, are respectively mediated by Mitf activation and Mitf downregulation, via the Akt-ERK-Mitf signaling pathway.

Example 8

The Effect of A3 Adenosine Receptor Ligands on Ex Vivo Human Skin Pigmentation

The results shown in FIGS. 8A-8E indicate that topical treatment of human skin explants with the A3 adenosine receptor antagonist MRS-1523 decreased melanin levels, whereas treatment with the A3 adenosine receptor agonist IB-MECA increased melanin levels, both after 12 days of exposure. It was further observed that hydroquinone, usually recognized as a whitening agent, increased skin pigmentation when applied topically at a concentration of 100 µM for 12 days.

Figure 8A:
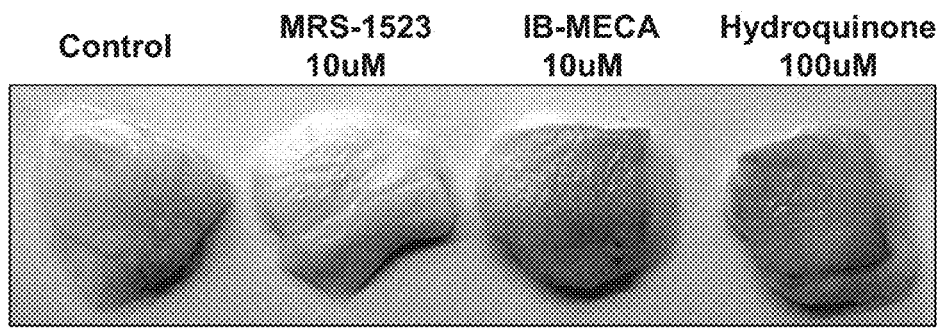
FIGS. 8A-8E shows the effect of A3 adenosine receptor ligands on skin pigmentation as evaluated by DOPA staining. Samples of human breast skin were topically treated with A3 adenosine receptor ligands (10 or 50 μM) or with hydroquinone (100 μM) as indicated three times over a culture period of 12 days, during which the medium was replaced every 3 days.
Figure 8B:
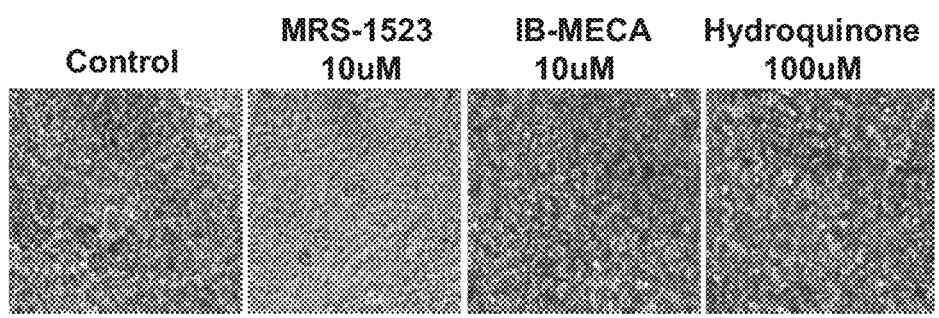
Figure 8C:
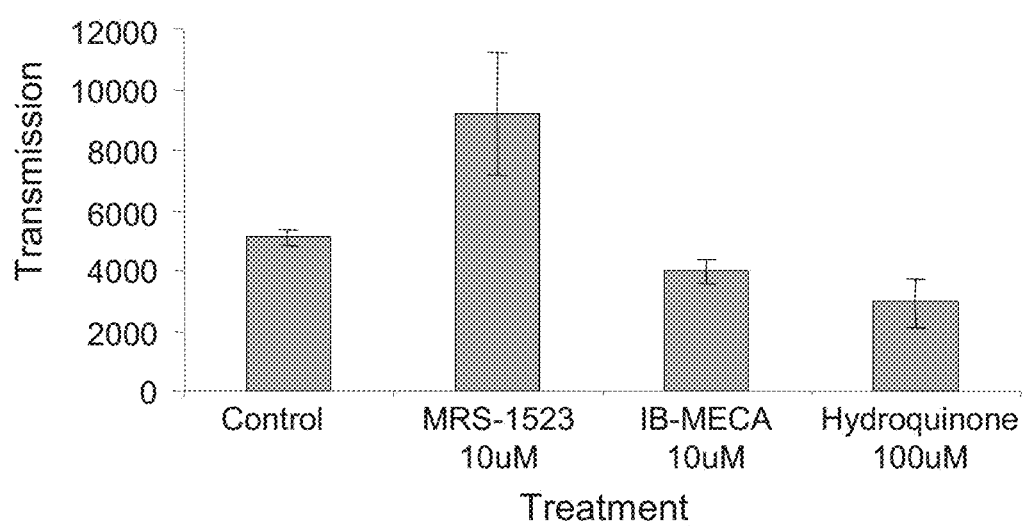
Figure 8D:
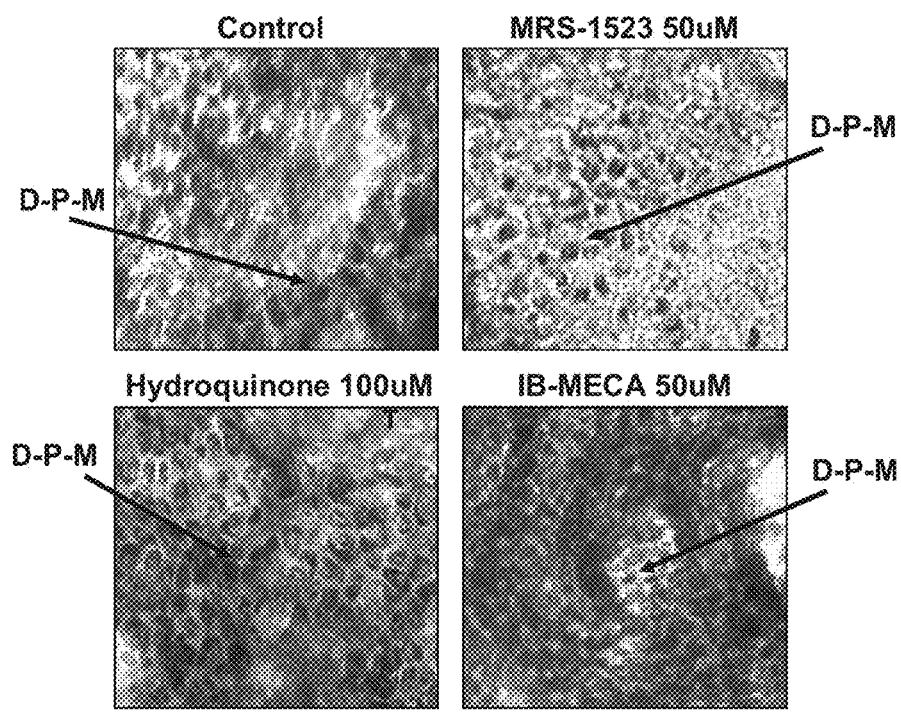

FIGS. 8B and 8D show the increased number of dark-stained DOPA positive melanocytes (D-P-M) in IB-MECA-treated and hydroquinone-treated samples as compared to control. FIGS. 8B and 8D further show the decreased number of D-P-M in MRS-1523-treated samples as compared to control.

Figure 8E:
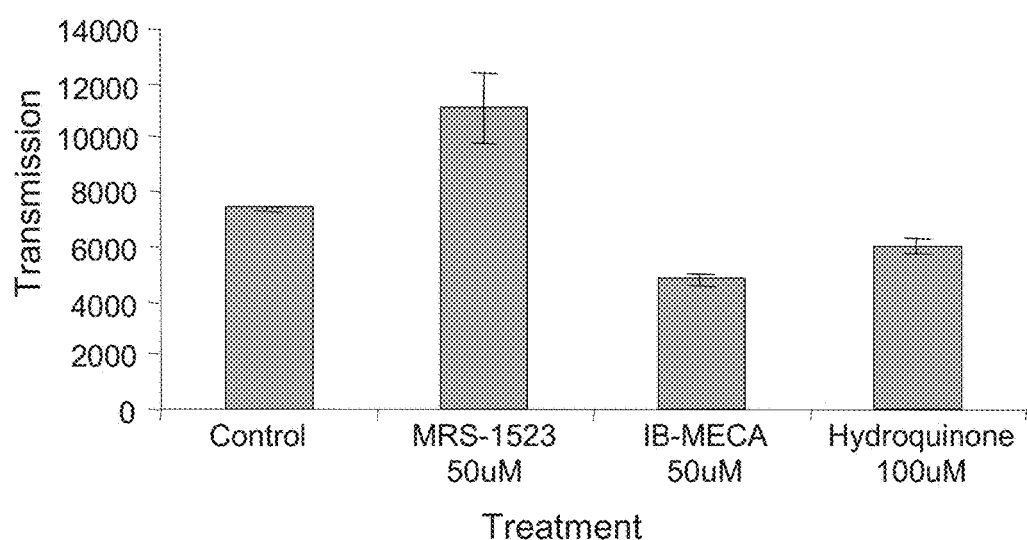

Evaluation of pigmentation level following DOPA staining, as measured by light transmission though the epidermal sheets, indicated that MRS-1523 decreased pigmentation by 80+21.8% and 49.5+6.9% respectively at ligand concentrations of 10 µM and 50 µM, whereas IB-MECA increased pigmentation by 27+3.9% and 36+2.6% respectively at concentrations of 10 µM and 50 µM (FIGS. 8C and 8E).

Example 9

Figure 9:
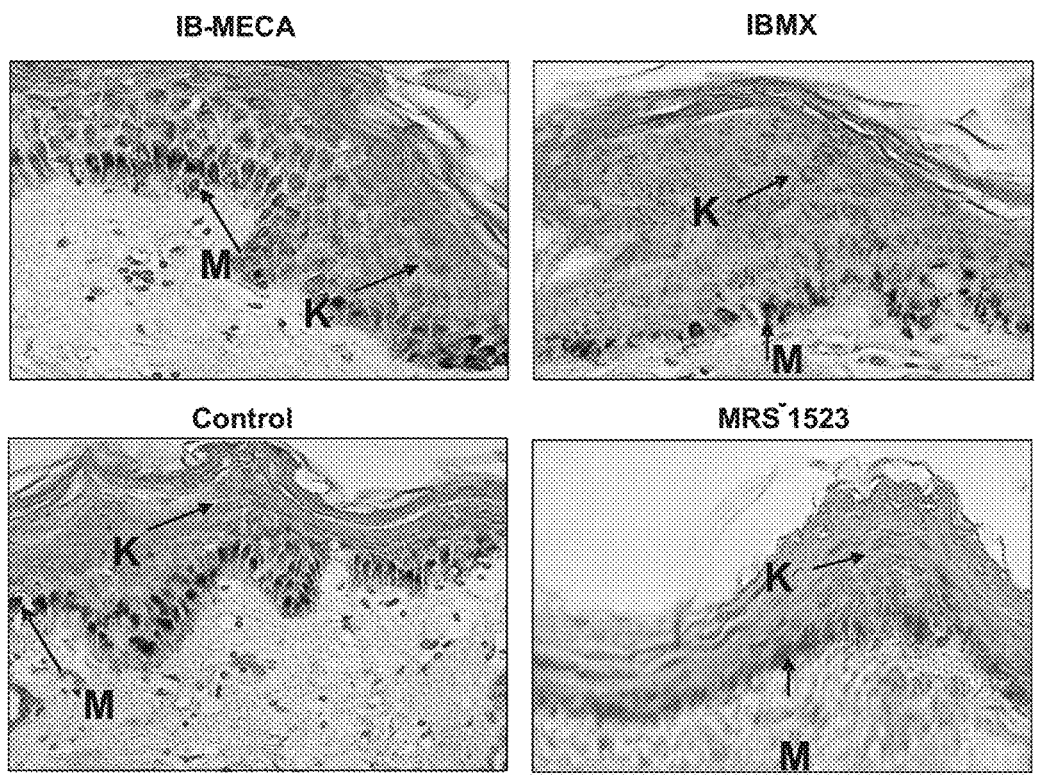
FIG. 9 shows the effect of A3 adenosine receptor ligands on skin pigmentation as evaluated by Fontana-Masson stain. Formalin fixed paraffin embedded skin sections from samples of human breast skin treated with IB-MECA, MRS-1523 or hydroquinone as described for FIG. 8, were evaluated for Fontana-Masson staining and visualized by light microscopy (×400). IBMX (100 μM) was used as a positive control for induction of melanogenesis. K, keratinocytes; M, melanocytes.

Effect of A3 Adenosine Receptor Ligands on Skin Pigmentation Evaluated by Fontana-Masson Stain Histological analysis of paraffin embedded and Fontana-Masson stained skin sections showed increased pigmentation in skin samples treated with the A3 adenosine receptor agonist IB-MECA (10 µM) or with the known melanogenesis enhancing agent 100 µM IBMX (100 µM) compared to control, and decreased pigmentation in skin samples treated with the A3 adenosine receptor antagonist MRS-1523 (FIG. 9). IBMX (3-isobutyl-1-methyl-xanthine) was used at a concentration of 100 µM as a positive control for achieving an enhanced pigmentation effect (see Gibbs et al., Pigment Cell Res. 2000 December; 13(6):458-66).

The histological appearance of IB-MECA-treated samples suggests that the observed increase in skin pigmentation is due to an elevation in melanin accumulation and/or deposition in the adjacent keratinocytes, rather than an increase in the number of melanocytes (see FIG. 9A). In contrast, the melanocytes in MRS-1523-treated cells appear to contain less melanin and there is a lesser extent of melanin accumulation and/or deposition in the keratinocytes (see FIG. 9D).

The results disclosed herein, which are based on observations in human skin, are consistent with the results of the in vitro studies described in Examples 1-3, showing elevation of melanin secretion into the extracellular medium following treatment with IB-MECA. That is, increased secretion may account for increased amounts of melanin deposited in the adjacent keratinocytes in the ex vivo human skin organ culture.

REFERENCES

Boissy R E, Visscher M, deLong M A: DeoxyArbutin: a novel revesible tyrosinase inhibitor with effective in vivo skin lightening potency. Exp Dermatol. 14:601-608, 2005.
Cardinali G, Ceccarelli S, Kovacs D, Aspite N, Lotti L V, Torrisi M R, Picardo M: Keratinocyte growth factor promotes melanosome transfer to keratinocytes. J Invest Dermatol. 2005 December; 125(6):1190-9.
Choi M Y, Song H S, Hur H S and Sim S S: Whitening activity of luteolin related to the inhibition of cAMP pathway in α-MSH-stimulated B16 melanoma cells. Arch Pharm Res 31(9):1166-1171, 2008.
Draelos Z D: Skin lightening preparations and the hydroquinone controversy. Dermatol Therap. 20:308-313, 2007.
Englaro W, Bertolotto, C, Busca R, Brunet A, Pages G, Ortonne J P and Ballotti R: Inhibition of mitogen-activated protein kinase pathway triggers B16 melanoma cell differentiation. J Biol Chem. 273:9966-9970, 1998.
Forsythe P, Ennis M., Inflam. Res. 48:301-7, 1999.
Fredholm B B, IJzerman A P, Jacobson K A, Klotz K N, Linden J. Pharmacol Rev. 2001 December; 53(4):527-52.
Fredholm B B, Arslan G, Halldner L, Kull B, Schulte G, Wasserman W Naunyn Schmiedebergs Arch Pharmacol. 2000 November; 362(4-5):364-74).
Hunt G, Todd C, Cresswell J E and Thody A J: Alpha melanocytes stimulating hormone and its analogue Nle4DPhe7 alpha-MSH affect morphology, tyrosinase activity and melanogenesis in cultured human melanocytes. J Cell Sci. 107:205-211, 1994.
Im S, Moro O, Peng F, Mederano E E, Cornelius J, Babcock G, Nordlund J J and Abdel-Malek Z A: Activation of cyclic AMP pathway by a-melanotropin mediates the response of human melanocytes to ultraviolet B radiation. Cancer Research 58: 47-54, 1998.
Lee J, Jung E, Lee J, Huh S, Boo Y C, Hyun C G, Kim Y-S, and Park D: Mecanosms of melanogenesis inhibition by 2,5-dimethyl-4-hydroxy-3(2H)-furanone. Br. J. Dermatol 157(2):242-8, 2007.
Liang B T, Jacobson K A. Proc. Natl. Acad. Sci. U.S.A. 95:6995-9, 1998.
Salvatore C A, Tilley S L, Latour A M, Fletcher D S, Koller B H, Jacobson M A, J. Biol. Chem. 275:4429-34, 2000.
Sato K., Takahshi H., Iraha R., and Toriyama M: Down-regulation of tyrosinase expression by acetylsalicylic acid in murine B16 melanoma. Biol Pharm Bull. 31(1) 33-37, 2008.

Slominski A, Tobin D J, Shibahara S, and Wortsman J: Melanin pigmentation in mammalian skin and its hormonal regulation. Physiol Rev. 84:1155-1224, 2004.

Von Lubitz D K, Eur. J. Pharmacol. 371:85-102, 1999.

Willis, I., Skin & Aging Supp., November 2000, 17-21.

Yao Y, Sei Y, Abbracchio M P, Jiang J L, Kim Y C, Jacobson K A Biochem. Biophys. Res. Comm 232:317-22, 1997.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method for decreasing melanin production, secretion, accumulation, or a combination thereof for treating or ameliorating a hyper-pigmentation skin condition or for cosmetic lightening of skin in a human subject, the method comprising contacting a skin cell with an effective amount of an A3 adenosine receptor antagonist, wherein the A3 adenosine receptor antagonist is selected from the group consisting of a dihydropyridine, a pyridine, a pyridinium salt, a triazoloquinazoline, an imidazoquinoline, an isoquinoline, a triazolopurine, a deazapurine, a pyrazolo-triazolo-pyrimidine, a triazolo-triazolo-pyrimidine, imidazolo-triazolo-pyrimidine, a xanthine, a flavonoid, and derivatives thereof, and wherein the skin condition is other than vitiligo.

2. The method according to claim 1, wherein said skin cell is a melanocyte or a keratinocyte.

3. The method according to claim 1, wherein said skin cell is within a tissue that comprises a plurality of melanocytes, keratinocytes, or both.

4. The method according to claim 1, wherein said A3 adenosine receptor antagonist decreases secretion of melanin from a melanocyte and accumulation of said melanin in a keratinocyte.

5. The method according to claim 1, wherein said A3 adenosine receptor antagonist is selected from the group consisting of:

3-propyl-6-ethyl-5[(ethylthio)carbonyl]-2-phenyl-4-propyl-3-pyridine carboxylate (MRS-1523);

1,4-dihydro-2-methyl-6-phenyl-4-(phenylethynyl)-3,5-pyridinedicarboxylic acid 3-ethyl-5-[(3-nitrophenyl) methyl] ester (MRS-1334);

3-ethyl-5-benzyl-2-methyl-4-phenylethynyl-6-phenyl-1,4-(±)-dihydropyridine-3,5 dicarboxylate (MRS-1191); and 3-ethyl-5-benzyl-2-methyl-6-phenyl-4-styryl-1,4-(±)-dihydropyridine-3,5-dicarboxylate (MRS-1097).

6. The method according to claim 1, further comprising contacting said skin cell with: hydroxytetronic acid, tetronic acid, hydroquinone, an α-hydroxy acid, a fatty acid ester of ascorbic acid, a tyrosinase inhibitor, a tyrosine phosphatase inhibitor, or any combination thereof.

7. The method according to claim 1 for treating or ameliorating a hyper-pigmentation skin condition in a human subject, wherein the hyper-pigmentation skin condition is selected from the group consisting of: pigmented spots, lentigo senilis, freckles, café au lait spots, liver spots, ephelides, periorbital darkening, post-inflammatory hyperpigmentation, pigmented keratosis, melasma, chloasma, and hyper-pigmentation due to a skin graft procedure.

8. The method according to claim 1, wherein said A3 adenosine receptor antagonist decreases melanin production in a melanocyte.

9. The method according to claim 1 for cosmetic lightening of skin in a human subject, the method comprising contacting a skin cell with an effective amount of an A3 adenosine receptor antagonist, wherein the A3 adenosine receptor antagonist is selected from the group consisting of a dihydropyridine, a pyridine, a pyridinium salt, a triazoloquinazoline, an imidazoquinoline, an isoquinoline, a triazolopurine, a deazapurine, a pyrazolo-triazolo-pyrimidine, a triazolo-triazolo-pyrimidine, imidazolo-triazolo-pyrimidine, a xanthine, a flavonoid, and derivatives thereof, and wherein the human subject is not suffering from vitiligo.

* * * * *